US010653684B2

(12) United States Patent
Dumas et al.

(10) Patent No.: US 10,653,684 B2
(45) Date of Patent: May 19, 2020

(54) ARYL UREAS WITH ANGIOGENISIS INHIBITING ACTIVITY

(71) Applicant: Bayer Healthcare LLC, Whippany, NJ (US)

(72) Inventors: Jacques Dumas, Carlisle, MA (US); William J. Scott, Guilford, CT (US); James Elting, Madison, CT (US); Holia Hatoum-Makdad, Hamden, CT (US)

(73) Assignee: Bayer Healthcare LLC, Whippany, NJ (US)

( * ) Notice: Subject to any disclaimer, the term of this patent is extended or adjusted under 35 U.S.C. 154(b) by 0 days.

(21) Appl. No.: 14/335,268

(22) Filed: Jul. 18, 2014

(65) Prior Publication Data

US 2016/0015697 A1   Jan. 21, 2016
US 2018/0296541 A9   Oct. 18, 2018

Related U.S. Application Data

(60) Continuation of application No. 11/932,626, filed on Oct. 31, 2007, now abandoned, which is a division of application No. 10/361,858, filed on Feb. 11, 2003, now Pat. No. 7,838,541.

(60) Provisional application No. 60/354,950, filed on Feb. 11, 2002.

(51) Int. Cl.
 *A61K 31/44* (2006.01)
(52) U.S. Cl.
 CPC ............. *A61K 31/44* (2013.01); *Y02A 50/411* (2018.01)
(58) Field of Classification Search
 None
 See application file for complete search history.

(56) References Cited

U.S. PATENT DOCUMENTS

| 8,841,330 B2 * | 9/2014 | Riedl | 514/350 |
| 2012/0093932 A1 * | 4/2012 | Li | A61K 9/0019 424/489 |
| 2012/0142742 A1 * | 6/2012 | Riedl | C07C 275/28 514/346 |

FOREIGN PATENT DOCUMENTS

| EP | 1 450 799 | 9/2004 |
| WO | 99/32106 A1 | 7/1999 |
| WO | 99/32111 A1 | 7/1999 |
| WO | 99/32436 A1 | 7/1999 |
| WO | 99/32455 A1 | 7/1999 |
| WO | 99/32463 A1 | 7/1999 |
| WO | 00/41698 A1 | 7/2000 |
| WO | 00/42012 A1 | 7/2000 |
| WO | 03/047579 A1 | 6/2003 |
| WO | 03/068228 A1 | 8/2003 |
| WO | 20061034797 A1 | 4/2006 |

OTHER PUBLICATIONS

Baek (Hepatology, 2008, 48, 1128-1137).*
Expired U.S. Appl. No. 60/334,609, filed Dec. 3, 2001.
Strumberg et al., "Phase I and Pharmacokinetic Study of the Raf Kinase Inhibitor Bay 42-9006 in Patients with Locally Advanced or Metastatic Cancer" Proceedings of the American Association for Cancer Research; Mar. 2001, 42, 543. #2921.
Eisenhauer et al., "Impact of new non-cytotoxics in the treatment of ovarian cancer", Int. J. Gynecol Cancer 2001, 11 (Suppl. 1) pp. 68-72.
Hotte et al., "BAY 43-9006: Early Clinical Data in Patients with Advanced Solid Malignancies", Current Pharmaceutical Design, 2002, 8, pp. 2249-2253.
Jacques Dumas, "Protein Kinase Inhibitors from the urea class" Current Opinion in Drug Discovery and Development, 2002 vol. 5, No. 5, pp. 718-727.
Hilger et al., "Inhibition of ERK phosphorylation and clinical outcome in patients treated with the Raf kinase inhibitor BAY 43-9006" 38th ASCO Meeting, Orlando FL, USA (002): 1916.
Moore et al., 38th ASCO Meeting, Orlando, Florida USA (2002): 1816.
Strumberg et al., 38th ASCO Meeting, Orlando, Florida USA (2002): 121.
Michael E. Aulton, "Pharmaceutics: The Science of Dosage Form Design", First Edition 1988, Chapter 13.
Submission Bayer to European Patent Office dated Sep. 28, 2010 in EP 05 797 740 (EP Regional Phase of WO 03/47579A1 / EP Patent EP1797038).
Submission Bayer to European Patent Office dated Sep. 12, 2011 in EP 05 797 740 (EP regional phase of WO 03/47579 A1).
Kubo et al., "Proceedings of the American Association for Cancer Research", vol. 43, 182, Mar. 2002, #913.
Meadows et al., "Mechanisms of Signal Transduction", Vascular Endothelial Growth Factor Induction of the Angiogenic Phenotype Requires Ras Activation, J. Biol. Chem. 2001, 276:49289-49298.
Bankston et al., "A Scaleable Synthesis of BAY 43-9006: A Potent Raf Kinase Inhibitor for the Treatment of Cancer", Organic Process Research & Development 2002, 6. pp. 777-781.
Schlingemann et al., "Role of Vascular Permeability Factor/ Vascular Endothelial Growth Factor in Eye Disease", British Journal of Ophthalmology, 1997, 81, pp. 501-512.
Aiello et al., "Vascular Endothelial Growth Factor in Ocular Fluid of Patients with Diabetic Retinopathy and Other Retinal Disorders", The New England Journal of Medicine, 1994, 331, 22, pp. 1480-1487.

* cited by examiner

*Primary Examiner* — Daniel M Podgorski

(74) *Attorney, Agent, or Firm* — Millen White Zelano and Branigan, PC

(57) ABSTRACT

This invention relates to methods of using aryl ureas to treat diseases mediated by the VEGF induced signal transduction pathway characterized by abnormal angiogenesis or hyperpermeability processes.

8 Claims, No Drawings

ARYL UREAS WITH ANGIOGENISIS INHIBITING ACTIVITY

FIELD OF THE INVENTION

This invention relates to methods of treating diseases mediated by the VEGF induced signal transduction pathway characterized by abnormal angiogenesis or hyperpermeability processes.

BACKGROUND OF THE INVENTION

Vasculogenesis involves the de novo formation of blood vessels from endothelial cell precursors or angioblasts. The first vascular structures in the embryo are formed by vasculogenesis. Angiogenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are highly specific for vascular endothelial cells (for reviews, see: Farrara et al. *Endocr. Rev.* 1992, 13, 18; Neufield et al. *FASEB J.* 1999, 13, 9).

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor-α and -β.

To date VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas fit-1 displays a weak response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1-2 mm. Oxygen and nutrients may be supplied to cells in tumor smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In sit hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 143I, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859) and several intracranial tumors (Plate et al. *Nature* 1992, 359, 845; Phillips et al. *Int. J. Oncol.* 1993, 2, 913; Berkman et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ.* 1995, 3, 315).

Over expression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, retinopathy of prematurity (Aiello et al. *New Engl. J. Med* 1994, 331, 1480; Peer et al. *Lab. Invest.* 1995, 72, 638), and age-related macular degeneration (AMD; see, Lopez et al. *Invest. Opthalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR leads to inhibition of VEGF-mediated angiogenesis and permeabilization, KDR inhibitors will be useful in treatment of diseases characterized by abnormal angiogenesis and/or hyperpermeability processes, including the above listed diseases

SUMMARY OF THE INVENTION

The present invention provides a method for treating diseases in humans or other mammals which are mediated by the VEGF induced signal transduction pathway, including those characterized by abnormal angiogenesis or hyperpermiability processes. These methods comprise administering a compound of formula I below or a salt, prodrug or stereoisomer thereof to a human or other mammal with a disease characterized by abnormal angiogenesis or hyperpermiability processes.

The compounds of formula I, which include all stereoisomeric forms (both isolated and in mixtures) salts thereof and prodrugs thereof are collectively referred to herein as the "compounds of the invention."

Formula I is as follows:

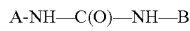 I wherein A is selected from the group consisting of (i) phenyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

(ii) naphthyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

(iii) 5 and 6 membered monocyclic heteroaryl groups, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro; and (iv) 8 to 10 membered bicyclic heteroaryl group in which the first ring is bonded to the NH of FIGURE I and contains 1-3 heteroatoms independently selected from the group consisting of O, N, and S, and the second ring is fused to the first ring using 3 to 4 carbon atoms. The bicyclic heteroaryl group is optionally substituted with 1-3 substituents independently selected from the group consisting of $R^1$, $OR^1$, $NR^1R^2$, $S(O)R^1$, $SO_2NR^1R^2$, $NR^1SO_2R^1$, $C(O)R^1$, $C(O)OR^1$, $C(O)NR^1R^2$, $NR^1C(O)R^2$, $NR^1C(O)OR^2$, halogen, cyano, and nitro.

B is selected from the group consisting of (i) phenyl, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro;

(ii) naphthyl, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro;

(iii) 5 and 6 membered monocyclic heteroaryl groups, having 1-3 heteroatoms independently selected from the group consisting of O, N and S, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro; and (iv) 8 to 10 membered bicyclic heteroaryl groups having 1-6 heteroatoms independently selected from the group consisting of O N and S, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro.

L is selected from the group consisting of:

(a) $-(CH_2)_m-O-(CH_2)_l-$,
(b) $-(CH_2)_m-(CH_2)_l-$,
(c) $-(CH_2)_m-C(O)-(CH_2)_l-$,
(d) $-(CH_2)_m-NR^3-(CH_2)_l-$,
(e) $-(CH_2)_m-NR^3C(O)-(CH_2)_l-$,
(f) $-(CH_2)_m-S-(CH_2)_l-$,
(g) $-(CH_2)_m-C(O)NR^3-(CH_2)_l-$,
(h) $-(CH_2)_m-CF_2-(CH_2)_l-$,
(i) $-(CH_2)_m-CCl_2-(CH_2)_l-$,
(j) $-(CH_2)_m-CHF-(CH_2)_l-$,
(k) $-(CH_2)_m-CH(OH)-(CH_2)_l-$;
(l) $-(CH_2)_m-C\equiv C-(CH_2)_l-$;
(m) $-(CH_2)_m-C\equiv C-(CH_2)_l$; and
(n) a single bond, where m and 1 are 0;
(o) $-(CH_2)_m-CR^4R^5-(CH_2)_l-$;

The variables m and 1 are integers independently selected from 0-4.

M is selected from the group consisting of:

(i) phenyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro;

(ii) naphthyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro;

(iii) 5 and 6 membered monocyclic heteroaryl groups, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro and also oxides (e.g. $=O$, $-O^-$ or $-OH$); and (iv) 8 to 10 membered bicyclic heteroaryl groups, having 1-6 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro and also oxides (e.g. $=O$, $-O^-$ or $-OH$).

(v) saturated and partially saturated $C_3$-$C_6$ monocyclic carbocyclic moiety optionally substituted with 1-3 substituents independently selected from the group consisting of $R^1$, $OR^1$, $NR^1R^2$, $S(O)R^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and, nitro;

(vi) saturated and partially saturated $C_8$-$C_{10}$ bicyclic carbocyclic moiety, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $-C(O)R^1$, $C(O)OR^1$, $C(O)NR^1R^2$, $NR^1C(O)R^2$, $NR^1C(O)OR^2$, halogen, cyano and nitro;

(vii) saturated and partially saturated 5 and 6 membered monocyclic heterocyclic moiety, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro, and also oxides (e.g. $=O$, $-O^-$ or $-OH$); and (viii) saturated and partially saturated 8 to 10 membered bicyclic heterocyclic moiety, having 1-6 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR'SO_2R^2$, $C(O)R^1$, $C(O)OR^1$, $C(O)NR^1R^2$, $NR^1C(O)R^2$, $NR^1C(O)OR^2$, halogen, cyano and nitro, and also oxides (e.g. $=O$, $-O^-$ or $-OH$).

Each $R^1$-$R^5$ are independently selected from the group consisting of:
(a) hydrogen,
(b) $C_1$-$C_6$ alkyl, preferably, $C_1$-$C_5$ linear, branched, or cyclic alkyl, wherein said alkyl is optionally substituted with halogen up to per-halo;
(c) phenyl;
(d) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S;
(e) $C_1$-$C_3$ alkyl-phenyl wherein said alkyl moiety is optionally substituted with halogen up to per-halo; and
(f) $C_1$-$C_3$ alkyl-heteroaryl having 1-4 heteroatoms selected from the group consisting of O, N and S, wherein said heteroaryl group is a 5-6 membered monocyclic heteroaryl or a 8-10 membered bicyclic heteroaryl, and wherein said alkyl moiety is optionally substituted with halogen up to per-halo.

Each $R^1$— $R^5$, when not hydrogen is optionally substituted with 1-3 substituents independently selected from the group consisting of $C_1$-$C_5$ linear branched or cyclic alkyl, wherein said alkyl is optionally substituted with halogen up to per-halo, $C_1$-$C_3$ alkoxy, wherein said alkoxy is optionally substituted with halogen up to per-halo, hydroxy, amino, $C_1$-$C_3$ alkylamino, $C_2$-$C_6$ dialkylamino, halogen, cyano, and nitro;

Each variable q is independently selected from 0, 1, or 2.

Suitable substituted and unsubstituted heteroaryl groups for the compounds of this invention, such as those for A, B and M of formula I, include, but are not limited to the following monocyclic heteroaryl groups:

2- and 3-furyl, 2- and 3-thienyl, 2- and 4-triazinyl, 1-, 2- and 3-pyrrolyl, 1-, 2-, 4- and 5-imidazolyl, 1-, 3-, 4- and 5-pyrazolyl, 2-, 4- and 5-oxazolyl, 3-, 4- and 5-isoxazolyl, 2-, 4- and 5-thiazolyl, 3-, 4- and 5-isothiazolyl, 2-, 3- and 4-pyridyl, 2-, 4-, 5- and 6-pyrimidinyl, 1,2,3-triazol-1-, -4- and -5-yl, 1,2,4-triazol-1-, -3- and -5-yl, 1- and 5-tetrazolyl, 1,2,3-oxadiazol-4- and -5-yl, 1,2,4-oxadiazol-3- and -5-yl, 1,3,4-thiadiazol-2- and -5-yl, 1,2,4-oxadiazol-3- and -5-yl, 1,3,4-thiadiazol-2- and -5-yl, 1,3,4-thiadiazol-3- and -5-yl, 1,2,3-thiadiazol-4- and -5-yl, 2-, 3-, 4-, 5- and 6-2H-thiopyranyl, 2-, 3- and 4-4H-thiopyranyl, 3- and 4-pyridazinyl, 2-,3-pyrazinyl,
and bicyclic heteroaryl groups such as:

Benzofuryl, benzothienyl, indolyl, benzimidazolyl, benzopyrazolyl, benzoxazolyl, benzisoxazolyl, benzothiazolyl, benzisothiazolyl, benz-1,3-oxadiazolyl, quinolinyl, isoquinolinyl, quinazolinyl, tetrahydroquinolinyl, tetrahydroisoquinolinyl, dihydrobenzofuryl, pyrazolo[3,4-b]pyrimidinyl, purinyl, benzodiazine, pteridinyl, pyrrolo[2,3-b]pyridinyl, pyrazolo[3,4-b]pyridinyl, oxazo[4,5-b]pyridinyl, imidazo[4,5-b]pyridinyl, cyclopentenopyridine, cyclohexanopyridine, cyclopentanopyrimidine, cyclohexanopyrimidine, cyclcopentanopyrazine, cyclohexanopyrazine, cyclopentanopyridiazine, cyclohexanopyridazine, cyclopentanoimidazole, cyclohexanoimidazole, cyclopentanothiophene and cyclohexanothiophene.

Suitable aryl groups which do not contain heteroatoms include, for example, phenyl and 1- and 2-naphthyl, tetrahydronaphthyl, indanyl, indenyl, benzocyclobtutanyl, benzocycloheptanyl and benzocycloheptenyl.

Suitable linear alkyl groups and alkyl portions of groups, e.g., alkoxy, alkylphenyl and alkylheteroaryl etc. throughout include methyl, ethyl, propyl, butyl, pentyl, etc. Suitable branched alkyl groups include all branched isomers such as isopropyl, isobutyl, sec-butyl, tert-butyl, etc.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety. Preferred halogens are Cl, Br and F.

The term "up to perhalo substituted linear and branched alkyl," includes alkyl groups having one alkyl hydrogen replaced with halogen, alkyl groups wherein all hydrogens are replaced with halogen, alkyl groups wherein more than one but less than all hydrogens are replaced by halogen and alkyl groups having alkyl hydrogens replaced by halogen and other substituents.

The term "cycloalkyl", as used herein, refers to cyclic structures having 3-8 members in the ring such as cyclopropyl, cyclobutyl and cyclopentyl and cyclic structures having 3-8 members with alkyl substituents such that, for example, "$C_3$ cycloalkyl" includes methyl substituted cyclopropyl groups.

The term "saturated carbocyclic moieties" defines only the cyclic structure, i.e. cyclopentyl, cyclohexyl, etc. Any alkyl substitution on these cyclic structures is specifically identified.

Saturated monocyclic and bicyclic carbocyclic moieties include cyclopropyl, cyclobutyl, cyclopentyl, cyclohexyl, and decahydronapthalene.

Partially saturated monocyclic and bicyclic carbocyclic moieties include cyclopentenyl, cyclohexenyl, cyclohexadienyl and tetrahydronaphthalene.

Saturated monocyclic and bicyclic heterocyclic moieties include tetrahydropyranyl, tetrahydrofuranyl, 1,3-dioxolane, 1,4-dioxanyl, morpholinyl, thiomorpholinyl, piperazinyl, piperidinyl, piperidinonyl, tetrahydropyrimidonyl, pentamethylene sulfide and tetramethylene sulfide.

Partially saturated monocyclic and bicyclic heterocyclic moieties include dihydropyranyl, dihydrofuranyl, dihydrothienyl, dihydropiperidinyl, and dihydropyrimidonyl.

A subclass of compounds of this invention is defined by formula I, wherein A B and M are selected from phenyl, naphthyl, furyl, isoindolinyl, oxadiazolyl, oxazolyl, isooxazolyl, pyrazolyl, pyridinyl, pyrimidinyl, pyrrolyl, quinolinyl, isoquinolinyl, tetrazolyl, thiadiazolyl, thiazolyl and thienyl and are optionally substituted as defined above.

Preferred substituents for B include methyl, trifluoromethyl, ethyl, n-propyl, n-butyl, n-pentyl, isopropyl, isobutyl, sec-butyl, tert-butyl, cyclopropyl, cyclobutyl, cyclopentyl, methoxy, ethoxy, propoxy, Cl, Br and F, cyano, nitro, hydroxy, amino, methylamino, dimethylamino, ethylamino and diethylamino as well as the structure -L-M.

Preferred substituents for A and M include methyl, trifluoromethyl, ethyl, n-propyl, n-butyl, n-pentyl, isopropyl, tert-butyl, sec-butyl, isobutyl, cyclopropyl, cyclobutyl, cyclopentyl, methoxy, ethoxy, propoxy, Cl, Br and F, cyano, nitro, hydroxy, amino, methylamino, dimethylamino, ethylamino and diethylamino and further include:

phenyl, pyridinyl, pyrimidinyl, chlorophenyl, dichlorophenyl, bromophenyl, dibromophenyl, chloropyridinyl, bromopyridinyl, dichloropyridinyl, dibromopyridinyl methylphenyl, methylpyridinyl quinolinyl, isoquinolinyl, isoindolinyl, pyrazinyl, pyridazinyl, pyrrolinyl, imidazolinyl, thienyl, furyl, isoxazolinyl, isothiazolinyl, benzopyridinyl, benzothiazolyl, $C_1$-$C_5$ acyl;
NH($C_1$-$C_5$ alkyl, phenyl or pyridinyl), such as aminophenyl;
N($C_1$-$C_5$ alkyl)($C_1$-$C_5$ alkyl, phenyl or pyridinyl), such as diethylamino and
dimethyl amino;

$S(O)_q$ ($C_1$-$C_5$ alkyl); such as methanesulfonyl;
$S(O)_q$H;
$SO_2NH_2$;
$SO_2NH(C_1$-$C_5$ alkyl);
$SO_2N(C_1$-$C_5$ alkyl)($C_1$-$C_5$ alkyl);
$NHSO_2(C_1$-$C_5$ alkyl); $N(C_1$-$C_3$ alkyl) $SO_2(C_1$-$C_5$ alkyl);
$CO(C_1$-$C_6$ alkyl or phenyl);
C(O)H;
$C(O)O(C_1$-$C_6$ alkyl or phenyl), such as $C(O)OCH_3$, —$C(O)OCH_2CH_3$, —
$C(O)OCH_2CH_2CH_3$;
C(O)OH;
$C(O)NH_2$ (carbamoyl);
$C(O)NH(C_1$-$C_6$ alkyl or phenyl), such as N-methylethyl carbamoyl, N-methyl carbamoyl, N-ethylcarbamoyl, or N-dimethylamino ethyl carbamoyl;
$C(O)N(C_1$-$C_6$ alkyl or phenyl)($C_1$-$C_6$ alkyl, phenyl or pyridinyl), such as N-dimethyl carbamoyl;
$C(N(C_1$-$C_5$ alkyl)) ($C_1$-$C_5$ alkyl);
$NHC(O)(C_1$-$C_6$ alkyl or phenyl) and
$N(C_1$-$C_5$ alkyl,)$C(O)(C_1$-$C_5$ alkyl).

Each of the above substituents is optionally partially or fully halogenated, such as difluoromethyl sulfonyl.

An embodiment of this invention includes the administration of compounds of this invention wherein in formula I, A, B and M follow one of the following of combinations:

A=phenyl, B=phenyl and M is phenyl, pyridinyl, quinolinyl, isoquinolinyl or not present, A=phenyl, B=pyridinyl and M is phenyl, pyridinyl, quinolinyl, isoquinolinyl or not present, A=phenyl, B=naphthyl and M is phenyl, pyridinyl, quinolinyl, isoquinolinyl or not present, A=pyridinyl, B=phenyl and M is phenyl, pyridinyl, quinolinyl, isoquinolinyl or not present, A=pyridinyl, B=pyridinyl and M is phenyl, pyridinyl, quinolinyl, isoquinolinyl or not present, A=pyridinyl, B=naphthyl and M is phenyl, pyridinyl, quinolinyl, isoquinolinyl or not present, A=isoquinolinyl, B=phenyl and M is phenyl, pyridinyl, quinolinyl, isoquinolinyl or not present, A=isoquinolinyl, B=pyridinyl and M is phenyl, pyridinyl, quinolinyl, isoquinolinyl or not present, A=isoquinolinyl, B=naphthyl and M is phenyl, pyridinyl, quinolinyl, isoquinolinyl or not present, A=quinolinyl, B=phenyl and M is phenyl, pyridinyl, quinolinyl, isoquinolinyl or not present, A=quinolinyl, B=pyridinyl and M is phenyl, pyridinyl, quinolinyl, isoquinolinyl or not present, A=quinolinyl, B=naphthyl and M is phenyl, pyridinyl, quinolinyl, isoquinolinyl or not present.

The structure L of formula I is preferably —O—, a single bond, —S—, —NH—, —N(CH$_3$)—, —NHCH$_2$—, —NC$_2$H$_4$—, —CH$_2$—, —C(O)—, —CH(OH)—, —NHC(O)N(CH$_3$)CH$_2$—, —N(CH$_3$)C(O)N(CH$_3$)CH$_2$—, —CH$_2$C(O)N(CH$_3$)—, —C(O)N(CH$_3$)CH$_2$—, —NHC(O)—, —N(CH$_3$)C(O)—, —C(O)N(CH$_3$)—, —C(O)NH—, —CH$_2$O—, —CH$_2$S—, —CH$_2$N(CH$_3$)—, —OCH$_2$, —CHF—, —CF$_2$—, —CCl$_2$—, —S—CH$_2$—, and —N(CH$_3$)CH$_2$—.

One of ordinary skill in the art will recognize that some of the compounds of Formula (I) can exist in different geometrical isomeric forms. A number of the compounds of Formula I possess asymmetric carbons and can therefore exist in racemic or optically active forms as well as in the form of racemic or non-racemic mixtures thereof and in the form of diastereomers and diastereomeric mixtures. All of these compounds, including cis isomers, trans isomers, diastereomic mixtures, racemates, non-racemic mixtures of enantiomers, substantially pure, and pure enantiomers, are considered to be within the scope of the present invention and are collectively referred to when reference is made to compounds of this invention.

Methods of separation of enantiomeric and diastereomeric mixtures are well known to one skilled in the art. The optical isomers can be obtained by resolution of the racemic mixtures according to conventional processes, for example, by the formation of diastereoisomeric salts using an optically active acid or base. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical chemical differences by methods known to those skilled in the art, for example, by chromatography or fractional crystallization. The optically active bases or acids are liberated from the separated diastereomeric salts.

Another process for separation of optical isomers involves the use of a chiral chromatography column (e.g., chiral HPLC columns) optimally chosen to maximize the separation of the enantiomers. Suitable chiral HPLC columns are manufactured by Diacel, e.g., Chiracel OD and Chiracel OJ. The optically active compounds of Formula (I) can likewise be obtained by utilizing optically active starting materials.

The present invention encompasses any isolated racemic or optically active form of compounds described in Formula I which possess angiogenesis inhibitory activity. The term stereoisomer is understood to encompass diastereoisomers, enantiomers, geometric isomers, etc. Herein, substantially pure enantiomers is intended to mean that no more than 5% w/w of the corresponding opposite enantiomer is present.

Pharmaceutically acceptable salts of these compounds as well as commonly used prodrugs of these compounds are also within the scope of the invention.

Salts are especially the pharmaceutically acceptable salts of compounds of formula (I) or such as, for example, organic or inorganic acid addition salts of compounds of formula (I). Suitable inorganic acids include but are not limited to halogen acids (such as hydrochloric acid and hydrobromic acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, trifluoroacetic acid, dodecanoic acid, glycolic acid, lactic acid, 2- or 3-hydroxybutyric acid, γ-aminobutyric acid (GABA), gluconic acid, glucosemonocarboxylic acid, benzoic acid, salicylic acid, phenylacetic acid and mandelic acid, fumaric acid, succinic acid, adipic acid, pimelic acid, suberic acid, azeiaic acid, malic acid, tartaric acid, citric acid, glucaric acid, galactaric acid, amino acids (such as glutamic acid, aspartic acid, N-methylglycine, acetytaminoacetic acid, N-acetylasparagine or N-acetylcysteine), pyruvic acid, acetoacetic acid, methanesulfonic acid, tri-fluoromethane sulfonic acid, 4-toluene sulfonic acid, benzenesulfonic acid, 1-naphthalenesulfonic acid, 2-naphthalenesulfonic acid, phosphoserine, and 2- or 3-glycerophosphoric acid.

In addition, pharmaceutically acceptable salts include acid salts of inorganic bases, such as salts containing alkaline cations (e.g., $Li^+$ $Na^+$ or K+), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4- diazabiclo[2.2.2]octane (DABCO), 1,5-diazabicyclo[4.3.0]non-5-ene (DBN) and 1,8-diazabicyclo[5.4.0]undec-7-ene (DBU).

The formation of prodrugs is well known in the art in order to enhance the properties of the parent compound; such properties include solubility, absorption, biostability and release time (see *Pharmaceutical Dosage Form and Drug Delivery Systems* (Sixth Edition), edited by Ansel et al, published by Williams & Wilkins, pages 27-29, (1995) which is hereby incorporated by reference). Commonly used prodrugs of the disclosed oxazolyl-phenyl-2,4-diamino-pyrimidine compounds are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see *Goodman and Gilman's The Pharmacological Basis of Therapeutics* (Ninth Edition), editor Molinoff et al., pub. by McGraw-Hill, pages 11-13, (1996), which is hereby incorporated by reference).

The invention also relates to methods for treating and preventing diseases, for example, angiogenesis disorders in mammals by administering a compound of this invention or a pharmaceutical composition comprising one or more compounds of this invention.

A compound according to the invention can be administered simultaneously with another angiogenesis inhibiting agent to a patient with such a disorder, in the same formulation or, more typically in separate formulations and, often, using different administration routes. Administration can also be sequentially, in any order.

A compound according to the invention can be administered in tandem with another angiogenesis inhibiting agent, wherein a compound according to the invention can be administered to a patient once or more per day for up to 28 consecutive days with the concurrent or intermittent administration of another angiogenesis inhibiting agent over the same total time period.

A compound according to the invention can be administered to a patient at an oral, intravenous, intramuscular, subcutaneous, or parenteral dosage which can range from about 0.1 to about 200 mg/kg of total body weight and the additional angiogenesis inhibiting agent can be administered to a patient at an intravenous, intramuscular, subcutaneous, or parenteral dosage which can range from about 0.1 mg to 200 mg/kg of patient body weight.

An embodiment of the present invention is a method for treating diseases in humans and/or other mammals which are mediated by the VEGF induced signal transduction pathway which comprises administering a compound of this invention to a human or other mammal.

Another embodiment of this invention is a method for treating diseases in humans and/or other mammals which are characterized by abnormal angiogenesis or hyperpermiability processes with a compound of this invention to a human or other mammal.

Another embodiment of this invention is a method for treating diseases in humans and/or other mammals which are characterized by abnormal angiogenesis or hyperpermiability processes, which are not raf-mediated, which comprises administering a compound of this invention to a human or other mammal.

Another embodiment of this invention is a method for treating diseases in humans and/or other mammals which are characterized by abnormal angiogenesis or hyperpermiability processes, which are not raf mediated or p38-mediated, which comprises administering a compound of this invention to a human or other mammal.

Another embodiment of this invention is a method for treating diseases in humans and/or other mammals which are characterized by abnormal angiogenesis or hyperpermiability processes, which are raf-mediated and/or p38 mediated, which comprises administering a compound of this invention to a human or other mammal.

Another embodiment of this invention is a method for treating one or more of the following conditions in humans and/or other mammals: tumor growth, retinopathy, including diabetic retinopathy, ischemic retinal-vein occlusion, retinopathy of prematurity and age related macular degeneration; rheumatoid arthritis, psoriasis, or bullous disorder associated with subepidermal blister formation, including bullous pemphigoid, erythema multiforme, or dermatitis herpetiformis, which comprises administering a compound of this invention to a human or other mammal with one or more of these conditions.

Another embodiment of this invention is a method for treating one or more of the following conditions in humans and/or other mammals: tumor growth, retinopathy, diabetic retinopathy, ischemic retinal-vein Occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis in combination with another condition selected from the group consisting of:

rheumatic fever, bone resorption, postmenopausal osteoporosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple, sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis) or complications due to total hip replacement. This method comprises administering a compound of this invention to a human or other mammal with one of the above combinations of conditions.

Another embodiment of this invention is a method for treating one or more of the following conditions in humans and/or other mammals:

tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis, in combination with an infectious disease selected from the group consisting of:

tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV). These methods comprise administering a compound of this invention to a human or other mammal with a combination of one of the above infectious diseases and one of the above diseases characterized by abnormal angiogenesis or hyperpermiability processes.

This invention further relates to kits comprising separate doses of the two mentioned chemotherapeutic agents in separate containers. The combinations of angiogenesis inhibiting agents can also be formed in vivo, e.g., in a patient's body.

These angiogenesis inhibiting agents can be administered in the conventional formulations and regimens in which they are known for use alone.

Conditions within a human or other mammal which can be treated by administering a compound of this invention are those characterized by abnormal angiogenesis or hyperpermiability processes. Conditions to be treated include tumor growth, retinopathy, including diabetic retinopathy, ischemic retinal-vein occlusion, retinopathy of prematurity and age related macular degeneration; rheumatoid arthritis, psoriasis, or a bullous disorder associated with subepidermal blister formation, including bullous pemphigoid, erythema multiforme, and dermatitis herpetiformis.

Methods of interest include the treatment of combinations of the conditions above (tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis) and another condition selected from the group consisting of:

rheumatic fever, bone resorption, postmenopausal osteoporosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis) or complications due to total hip replacement.

Also provided is a method for treating combinations of the conditions above (tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis) and an infectious disease selected from the group consisting of:

tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV).

The compounds of this invention can be made according to conventional chemical methods, and/or as disclosed below, from starting materials which are either commercially available or producible according to routine, conventional chemical methods. General methods for the preparation of the compounds are given below, and the preparation of a suitable compound is specifically illustrated in the Examples.

Ureas of formula (I) can be prepared by a variety of simple methods known in the art. General approaches for the formation of those compounds can be found in "*Advanced Organic Chemistry*", by J. March, John Wiley and Sons, 1985 and in "*Comprehensive Organic Transformations*", by R. C. Larock, VCH Publishers, 1989), which are hereby incorporated by reference. Nevertheless, the following general preparative methods are presented to aid one of skill in the art in synthesizing these compounds, with more detailed examples being presented in the experimental section describing the working examples.

General Preparative Methods

Heterocyclic amines may be synthesized utilizing known methodology (Katritzky, et al. *Comprehensive Heterocyclic Chemistry*; Permagon Press: Oxford, UK (1984). March. *Advanced Organic Chemistry*, $3^{rd}$ Ed.; John Wiley: New York (1985)). For example, as shown in Scheme I, 5-aminopyrazoles substituted at the N–1 position with either aryl or heteroaryl moieties may be synthesized by the reaction of an α-cyanoketone (2) with the appropriate aryl- or heteroaryl hydrazine (3, $R^2$=aryl or heteroaryl). Cyanoketone 2, in turn, is available from the reaction of acetamidate ion with an appropriate acyl derivative, such as an ester, an acid halide, or an acid anhydride. In cases where the $R^2$ moiety offers suitable anion stabilization, 2-aryl- and 2-heteroarylfurans may be synthesized from a Mitsunobu reaction of cyanoketone 2 with alcohol 5, followed by base catalyzed cyclization of enol ether 6 to give furylamine 7.

Scheme I. Selected General Methods for Heterocyclic Amine Synthesis

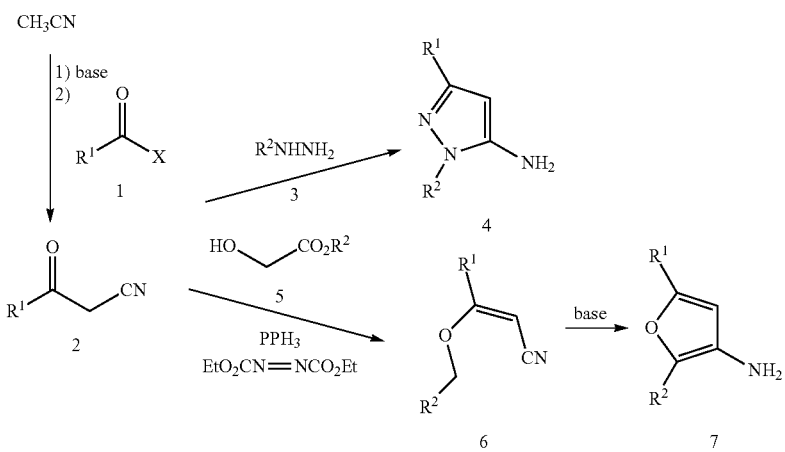

Substituted anilines may be generated using standard methods (March. *Advanced Organic Chemistry*, 3<sup>rd</sup> Ed.; John Wiley: New York (1985). Larock. *Comprehensive Organic Transformations*; VCH Publishers: New York (1989)). As shown in Scheme II, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino-and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3<sup>rd</sup> Ed.; John Wiley: New York (1985). Larock. *Comprehensive Organic Transformations*; VCH Publishers: New York (1989)).

Scheme II Reduction of Nitroaryls to Aryl Amines

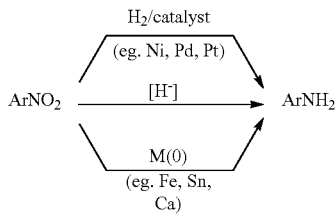

Nitroaryls are commonly formed by electrophilic aromatic nitration using $HNO_3$, or an alternative $NO_2^+$ source. Nitro aryls may be further elaborated prior to reduction. Thus, nitroaryls substituted with

potential leaving groups (eg. F, Cl, Br, etc.) may undergo substitution reactions on treatment with nucleophiles, such as thiolate (exemplified in Scheme III) or phenoxide. Nitroaryls may also undergo Ullmnan-type coupling reactions (Scheme III).

Scheme III Selected Nucleophilic Aromatic Substitution using Nitroaryls

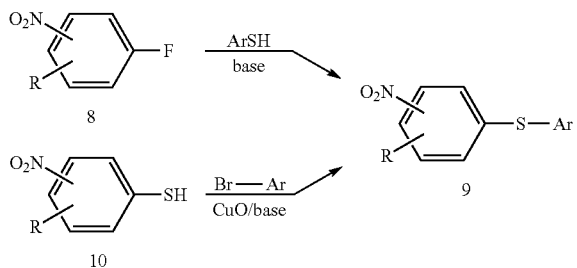

As shown in Scheme IV, urea formation may involve reaction of a heteroaryl isocyanate (12) with an aryl amine (11). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent. A urea may also be generated from the reaction of an aryl isocyanate (15) with a heterocyclic amine.

Scheme IV Selected Methods of Urea Formation (Het = heterocycle)

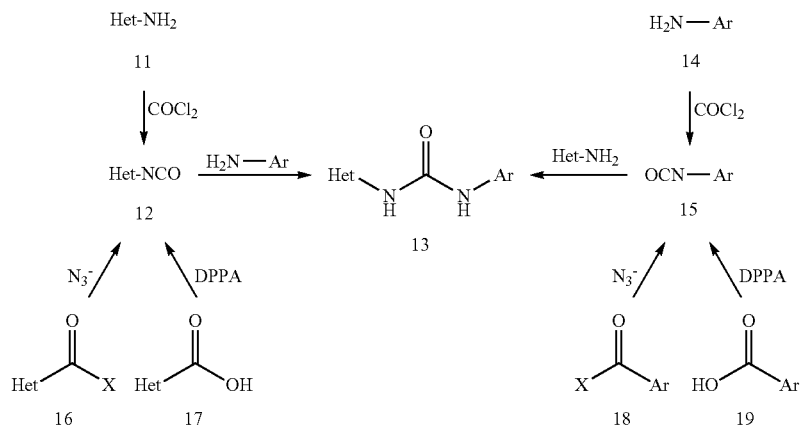

Finally, ureas may be further manipulated using methods familiar to those skilled in the art. For example, 2-aryl and 2-heteroarylthienyl ureas are available from the corresponding 2-halothienyl urea through transition metal mediated cross coupling reactions (exemplified with 2-bromothiophene 25, Scheme V). Thus, reaction of nitrile 20 with an α-thioacetate ester gives 5-substituted-3-amino-2-thiophenecarboxylate 21 (Ishizaki et al. JP 6025221). Decarboxylation of ester 21 may be achieved by protection of the amine, for example as the tert-butoxy (BOC) carbamate (22), followed by saponification and treatment with acid. When BOC protection is used, decarboxylation may be accompanied by deprotection giving the substituted 3-thiopheneammonium salt 23. Alternatively, ammonium salt 23 may be directly generated through saponification of ester 21 followed by treatment with acid. Following urea formation as described above, bromination affords penultimate halothiophene 25. Palladium mediated cross coupling of thiophene 25 with an appropriate tributyl- or trimethyltin ($R^2$=aryl or heteroaryl) then affords the desired 2-aryl- or 2-heteroarylthienyl urea.

Scheme V Synthesis and Interconversion of Ureas

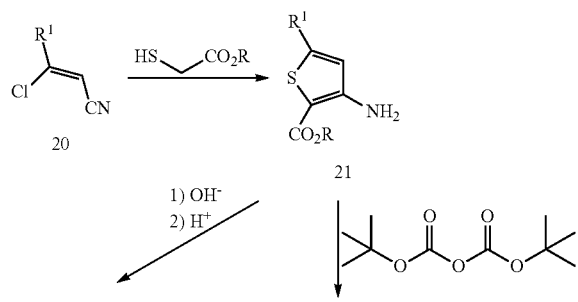

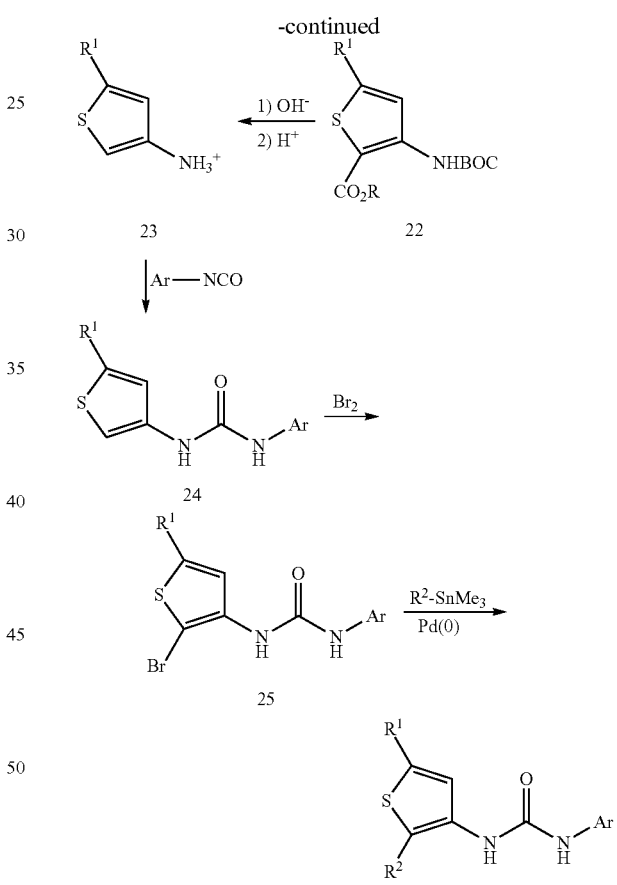

Finally, ureas may be further manipulated using methods familiar to those skilled in the art.

The compounds may be administered orally, topically, parenterally, by inhalation or spray or vaginally, sublingually, or rectally in dosage unit formulations.

The term 'administration by injection' includes intravenous, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, microcrystalline cellulose, carboxymethyl cellulose, hydroxypropylmethylcellulose or alginic acid; and binding agents, for example magnesium stearate, stearic acid or talc and lubricants/surfactants such as sodium lauryl sulfate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administrated transdermally using methods known to those skilled in the art (see, for example: Chien; "Transdermal Controlled Systemic Medications"; Marcel Dekker, Inc.; 1987. Lipp et al. WO94/04157 3 Mar. 94). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene coploymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily vaginal dosage regimen will preferably be from 0.01 to 200 mg/Kg of total body weight. The daily rectal dosage regime will preferably be from 0.01 to 200 mg/Kg of total body weight. The daily topical dosage regime will preferably be from 0.1 to 200 mg administered between one to four times daily. The transdermal concentration will preferably be that required to maintain a daily dose of from 0.01 to 200 mg/Kg. The daily inhalation dosage regime will preferably be from 0.01 to 10 mg/Kg of total body weight. These dosages regimes can be achieved with multiple dosages within a single day or extended dosages, such as those given on a weekly or monthly basis.

It will be appreciated by those skilled in the art that the particular method of administration will depend on a variety of factors, all of which are considered routinely when administering therapeutics. It will also be appreciated by one skilled in the art that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy.

It will be further appreciated by one skilled in the art that the optimal course of treatment, i.e., the mode of treatment and the daily number of doses of a compound of this invention given for a defined number of days, can be ascertained by those skilled in the art using conventional treatment tests.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

Specific preparations of the compounds of this invention are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al, "Inhibition of RAF Kinase Activity using Substituted Heterocyclic Ureas" PCT Int. Appl., WO 99 32106, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCP Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698.

Methods for preparing the compounds of this invention are also described in the following U.S. applications, some of which correspond to the PCT applications listed above.
Ser. No. 08/863,022, filed May 23, 1997;
Ser. No. 08/996,344, filed Dec. 22, 1997;
Ser. No. 08/996,343, filed Dec. 22, 1997;
Ser. No. 08/996,181, filed Dec. 22, 1997;
Ser. No. 08/995,749, filed Dec. 22, 1997;
Ser. No. 08/995,750, filed Dec. 22, 1997;
Ser. No. 08/995,751, filed Dec. 22, 1997;
Ser. No. 09/083,399, filed May 22, 1998;
Ser. No. 09/425,228, filed Oct. 22, 1999;
Ser. No. 09/777,920, filed Feb. 7, 2001.
Ser. No. 09/722,418 filed Nov. 28, 2000
Ser. No. 09/838,285, filed Apr. 20, 2001;
Ser. No. 09/838,286, filed Apr. 20, 2001;
Ser. No. 09/458,548, filed Jan. 12, 2001;
Ser. No. 09/948,915, filed Sep. 10, 2001, and
Ser. No. (attorney docket number. Bayer 34 V1), filed Dec. 3, 2001.

The entire disclosure of all applications, patents and publications cited above and below are hereby incorporated by reference.

The compounds of this invention are producible from known compounds (or from starting materials which, in turn, are producible from known compounds), e.g., through the general preparative methods shown below. The activity of a given compound to inhibit angiogenesis activity can be routinely assayed, e.g., according to procedures disclosed below.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever. The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg.

All temperatures are reported uncorrected in degrees Celsius (° C.). Unless otherwise indicated, all parts and percentages are by weight.

Commercial grade reagents and solvents were used without further purification.

Thin-layer chromatography (TLC) was performed on Whatman pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Proton ($^1$H) nuclear magnetic resonance (NMR) spectra were measured with a General Electric GN-Omega 300 (300 MHz) spectrometer with either Me$_4$Si (δ 0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer.

Chemical ionization mass spectra (CI-MS) were obtained using a Hewlett Packard MS-Engine (5989A) with methane as the reagent gas (1×10$^4$ torr to 2.5×10$^4$ torr). The direct insertion desorption chemical ionization (DCI) probe (Vacumetrics, Inc.) was ramped from 0-1.5 amps in 10 sec and held at 10 amps until all traces of the sample disappeared (~1-2 min). Spectra were scanned from 50-800 amu at 2 sec per scan. HPLC—electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source.

Gas chromatography—ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV).

Elemental analyses were conducted by Robertson Microlit Labs, Madison N.J. All compounds displayed NMR spectra, LRMS and either elemental analysis or HRMS consistent with assigned structures.

LIST OF ABBREVIATIONS AND ACRONYMS

AcOH acetic acid anh anhydrous

BOC tert-butoxycarbonyl conc concentrated dec decomposition

DMPU 1,3-dimethyl-3,4,5,6-tetrahydro-2(1H)-pyrimidinone

DMF N,N-dimethylformamide

DMSO dimethylsulfoxide

DPPA diphenylphosphoryl azide

EtOAc ethyl acetate

EtOH ethanol (100%)

Et$_2$O diethyl ether

Et$_3$N triethylamine m-CPBA 3-chloroperoxybenzoic acid

MeOH methanol pet. ether petroleum ether (boiling range 30-60° C.)

THF tetrahydrofuran

TFA trifluoroacetic acid.

Tf trifluoromethanesulfonyl

Example A

N-[4-chloro-3-(trifluoromethyl)phenyl]-N'-{4-[2-carbamoyl-(4-yridyloxy)]phenyl}urea Step 1: Preparation of 4-chloro-2-pyridinecarboxamide

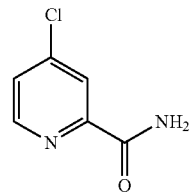

To a stirred mixture of methyl 4-chloro-2-pyridinecarboxylate hydrochloride (1.0 g, 4.81 mmol) dissolved in conc. aqueous ammonia (32 mL) was added ammonium chloride (96.2 mg, 1.8 mmol, 0.37 equiv.), and the heterogeneous reaction mixture was stirred at ambient temperature for 16 h. The reaction mixture was poured into EtOAc (500 mL) and water (300 mL). The organic layer was washed with water (2×300 mL) and a saturated NaCl solution (1×300 mL), dried (MgSO$_4$), concentrated in vacuo to give 4-chloro-2-pyridinecarboxamide as a beige solid (604.3 mg, 80.3%): TLC (50% EtOAc/hexane) R$_f$ 0.20; $^1$H-NMR (DMSO-d$_6$) δ 8.61 (d, J=5.4 Hz, 1H), 8.20 (broad s, 1H), 8.02 (d, J=1.8 Hz, 1H), 7.81 (broad s, 1H), 7.76 to 7.73 (m, 1H).

Step 2: Preparation of 4-(4-aminophenoxy)-2-pyridinecarboxamide

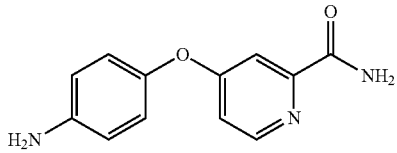 [SMILES: NC(=O)c1cc(Oc2ccc(N)cc2)ccn1]

To 4-aminophenol (418 mg, 3.83 mmol) in anh DMF (7.7 mL) was added potassium tert-butoxide (447 mg, 3.98 mmol, 1.04 equiv.) in one portion. The reaction mixture was stirred at room temperature for 2 h, and a solution of 4-chloro-2-pyridinecarboxamide (600 mg, 3.83 mmol, 1.0 equiv.) in anh DMF (4 mL) was then added. The reaction mixture was stirred at 80° C. for 3 days and poured into a mixture of EtOAc and a saturated NaCl solution. The organic layer was sequentially washed with a saturated NH$_4$Cl solution then a saturated NaCl solution, dried (MgSO$_4$), and concentrated under reduced pressure. The crude product was purified using MPLC chromatography (Biotage®; gradient from 100% EtOAc to followed by 10% MeOH/50% EtOAc/40% hexane) to give the 4-chloro-5-trifluoromethylaniline as a brown solid (510 mg, 58%). $^1$H-NMR (DMSO-d$_6$) δ 8.43 (d, J=5.7 Hz, 1H), 8.07 (br s, 1H), 7.66 (br s, 1H), 7.31 (d, J=2.7 Hz, 1H), 7.07 (dd, J=5.7 Hz, 2.7 Hz, 1H), 6.85 (d, J=9.0 Hz, 2H), 6.62 (d, J=8.7 Hz, 2H), 5.17 (broad s, 2H); HPLC EI-MS m/z 230 ((M+H).

Step 3: Preparation of N-[4-chloro-3-(trifluoromethyl)phenyl]-N'-{4-[2-carbamoyl-(4-pyridyloxy)]phenyl}urea

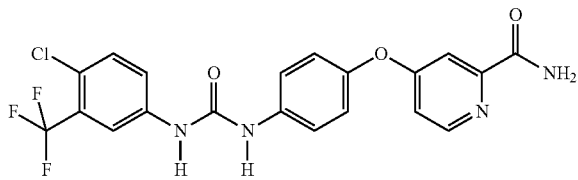 [SMILES: NC(=O)c1cc(Oc2ccc(NC(=O)Nc3ccc(Cl)c(C(F)(F)F)c3)cc2)ccn1]

A mixture of 4-chloro-5-trifluoromethylaniline (451 mg, 2.31 mmol, 1.1 equiv.) and 1,1'-carbonyl diimidazole (419 mg, 2.54 mmol, 1.2 equiv.) in anh dichloroethane (5.5 mL) was stirred under argon at 65° C. for 16 h. Once cooled to room temperature, a solution of 4-(4-aminophenoxy)-2-pyridinecarboxamide (480 mg, 2.09 mmol) in anh THF (4.0 mL) was added, and the reaction mixture was stirred at 60° C. for 4 h. The reaction mixture was poured into EtOAc, and the organic layer was washed with water (2×) and a saturated NaCl solution (1×), dried (MgSO$_4$), filtered, and evaporated in vacuo. Purification using MPLC chromatography (Biotage®; gradient from 100% EtOAc to 2% MeOH/EtOAc) gave N-[4-chloro-3-(trifluoromethyl)phenyl]-N'-{4-[2-carbamoyl-(4-pyridyloxy)]phenyl}urea as a white solid (770 mg, 82%): TLC (EtOAc) R$_f$ 0.11, 100% ethyl acetate $^1$H-NMR (DMSO-d) δ 9.21 (s, 1H), 8.99 (s, 1H), 8.50 (d, J=5.6 Hz, 1H), 8.11 (s, 1H), 8.10 (s, 1H), 7.69 (broad s, 1H), 7.64 (dd, J=8.2 Hz, 2.1 Hz, 1H), 7.61 (s, 1H), 7.59 (d, J=8.8 Hz, 2H), 7.39 (d, J=2.5 Hz, 1H), 7.15 (d, J=8.9 Hz, 2H), 7.14 (m, 1H); MS LC-MS (MH$^+$=451). Anal. calcd for C$_{20}$H$_{14}$ClF$_3$N$_4$O$_3$: C, 53.29%; H, 3.13%; N, 12.43%. Found: C, 53.33%; H, 3.21%; N, 12.60%.

Example B

N-[4-chloro-3-(trifluoromethyl)phenyl]-N'-{4-[2-N-methylcarbamoyl-4-pyridyloxy]phenyl}urea

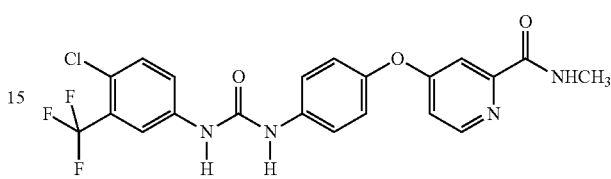

Step 1: 4-Chloro-N-methyl-2-pyridinecarboxamide is first synthesized from 4-chloropyridine-2-carbonyl chloride by adding 4-chloropyridine-2-carbonyl chloride HCl salt (7.0 g, 32.95 mmol) in portions to a mixture of a 2.0 M methylamine solution in THF (100 mL) and MeOH (20 mL) at 0° C. The resulting mixture is stored at 3° C. for 4 h, then concentrated under reduced pressure. The resulting nearly dry solids are suspended in EtOAc (100 mL) and filtered. The filtrate is washed with a saturated NaCl solution (2×100 mL), dried (Na$_2$SO$_4$) and concentrated under reduced pressure to provide 4-chloro-N-methyl-2-pyridinecarboxamide as a yellow, crystalline solid.

Step 2: A solution of 4-aminophenol (9.60 g, 88.0 mmol) in anh. DMF (150 mL) is treated with potassium tert-butoxide (10.29 g, 91.7 mmol), and the reddish-brown mixture is stirred at room temp. for 2 h. The contents are treated with 4-chloro-N-methyl-2-pyridinecarboxamide (15.0 g, 87.9 mmol) from Step 1 and K$_2$CO$_3$ (6.50 g, 47.0 mmol) and then heated at 80° C. for 8 h. The mixture is cooled to room temp. and separated between EtOAc (500 mL) and a saturated NaCl solution (500 mL). The aqueous phase is back-extracted with EtOAc (300 mL). The combined organic layers are washed with a saturated NaCl solution (4×1000 mL), dried (Na$_2$SO$_4$) and concentrated under reduced pressure. The resulting solids are dried under reduced pressure at 35° C. for 3 h to afford 4-(2-(N-methylcarbamoyl)-4-pyridyloxy)aniline as a light-brown solid. $^1$H-NMR (DMSO-d) δ 2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

Step 3: A solution of 4-chloro-3-(trifluoromethyl)phenyl isocyanate (14.60 g, 65.90 mmol) in CH$_2$Cl$_2$ (35 mL) is added dropwise to a suspension of 4-(2-(N-methylcarbamoyl)-4-pyridyloxy)aniline from Step 2; (16.0 g, 65.77 mmol) in CH$_2$Cl$_2$ (35 mL) at 0° C. The resulting mixture is stirred at room temp. for 22 h. The resulting yellow solids are removed by filtration, then washed with CH$_2$Cl$_2$ (2×30 mL) and dried under reduced pressure (approximately 1 mmHg) to afford N-(4-chloro-3-(trifluoromethyl)phenyl)-N'-(4-(2-(N-methylcarbamoyl)-4-pyridyloxy)phenyl) urea as an off-white solid: mp 207-209° C.; $^1$H-NMR (DMSO-d$_6$) δ 2.77 (d, J=4.8 Hz, 3H), 7.16 (m, 3H), 7.37 (d, J=2.5 Hz, 1H), 7.62 (m, 4H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 465 ((M+H)$^+$).

Example C

N-[2-methoxy-5-(trifluoromethyl)phenyl]-N'-{4-[2-N-methylcarbamoyl-4-pyridyloxy]phenyl}urea

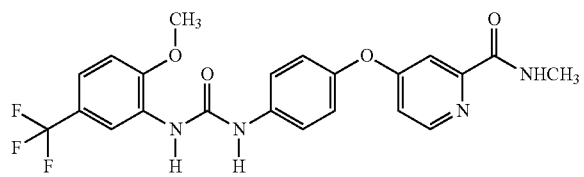 [SMILES: CNC(=O)c1cc(Oc2ccc(NC(=O)Nc3cc(C(F)(F)F)ccc3OC)cc2)ccn1]

Step 1: 4-Chloro-N-methyl-2-pyridinecarboxamide is first synthesized from 4-chloropyridine-2-carbonyl chloride by adding 4-chloropyridine-2-carbonyl chloride HCl salt (7.0 g, 32.95 mmol) in portions to a mixture of a 2.0 M methylamine solution in THF (100 mL) and MeOH (20 mL) at 0° C. The resulting mixture is stored at 3° C. for 4 h, then concentrated under reduced pressure. The resulting nearly dry solids are suspended in EtOAc (100 mL) and filtered. The filtrate is washed with a saturated NaCl solution (2×100 mL), dried ($Na_2SO_4$) and concentrated under reduced pressure to provide 4-chloro-N-methyl-2-pyridinecarboxamide as a yellow, crystalline solid.

Step 2: A solution of 4-aminophenol (9.60 g, 88.0 mmol) in anh. DMF (150 mL) is treated with potassium tert-butoxide (10.29 g, 91.7 mmol), and the reddish-brown mixture is stirred at room temp. for 2 h. The contents are treated with 4-chloro-N-methyl-2-pyridinecarboxamide (15.0 g, 87.9 mmol) from Step 1 and $K_2CO_3$ (6.50 g, 47.0 mmol) and then heated at 80° C. for 8 h. The mixture is cooled to room temp. and separated between EtOAc (500 mL) and a saturated NaCl solution (500 mL). The aqueous phase is back-extracted with EtOAc (300 mL). The combined organic layers are washed with a saturated NaCl solution (4×1000 mL), dried ($Na_2SO_4$) and concentrated under reduced pressure. The resulting solids are dried under reduced pressure at 35° C. for 3 h to afford 4-(2-(N-methylcarbamoyl)-4-pyridyloxy)aniline as a light-brown solid. $^1$H-NMR (DMSO-$d_6$) δ 2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

Step 3: To a solution of 2-methoxy-5-(trifluoromethyl) aniline (0.15 g) in anh $CH_2Cl_2$ (15 mL) at 0° C. is added CDI (0.13 g). The resulting solution is allowed to warm to room temp. over 1 h, is stirred at room temp. for 16 h, then is treated with 4-(2-(N-methylcarbamoyl)-4-pyridyloxy)aniline (0.18 g) from Step 2. The resulting yellow solution is stirred at room temp. for 72 h, then is treated with $H_2O$ (125 mL). The resulting aqueous mixture is extracted with EtOAc (2×150 mL). The combined organics are washed with a saturated NaCl solution (100 mL), dried ($MgSO_4$) and concentrated under reduced pressure. The residue is triturated (90% EtOAc/10% hexane). The resulting white solids are collected by filtration and washed with EtOAc. The filtrate is concentrated under reduced pressure and the residual oil purified by column chromatography (gradient from 33% EtOAc/67% hexane to 50% EtOAc/50% hexane to 100% EtOAc) to give N-(2-methoxy-5-(trifluoromethyl) phenyl)-N'-(4-(2-(N-methylcarbamoyl)-4-pyridyloxy)phenyl) urea as a light tan solid: TLC (100% EtOAc) $R_f$ 0.62; $^1$H NMR (DMSO-d) δ 2.76 (d, J=4.8 Hz, 3H), 3.96 (s, 3H), 7.1-7.6 and 8.4-8.6 (m, 11H), 8.75 (d, J=4.8 Hz, 1H), 9.55 (s, 1H); FAB-MS m/z 461 ((M+H)$^+$).

Biological Examples

KDR (VEGFR2 Assay:

The cytosolic kinase domain of KDR kinase was expressed as a 6His fusion protein in Sf9 insect cells. The KDR kinase domain fusion protein was purified over a Ni++ chelating column. Ninety-six well ELISA plates Were coated with 5 μl HEPES buffer (20 mM poly(Glu4; Tyr1) (Sigma Chemical Co., St. Louis, Mo.) in 100 μk HEPES buffer (20 mM HEPES, pH 7.5, 150 mM Na Cl, 0.02% Thimerosal) at 4° overnight. Before use, the plate was washed with HEPES, NaCl buffer and the plates were blocked with 1% BSA, 0.1% Tween 20 in HEPES, NaCl buffer.

Test compounds were serially diluted in 100%/DMSO form 4 mM to 0.12 μM in half-log dilutions. These dilutions were further diluted twenty fold in $H_2O$ to obtain compound solutions in 5% DMSO. Following loading of the assay plate with 85 μl of assay buffer (20 mM HEPES, pH 7.5, 100 mM KCl, 10 mM $MgCl_2$, 3 mM $MnCl_2$, 0.05% glycerol, 0.005% Triton X-100, 1 mM-mercaptoethanol, with or without 3.3 μM ATP), 5 μl of the diluted compounds were added to a final assay volume of 100 μl. Final concentrations were between 10 μM, and 0.3 mM in 0.25% DMSO. The assay was initiated by the addition of 10 μl (30 ng) of KDR kinase domain.

The assay was incubated with test compound or vehicle alone with gentle agitation at room temperature for 60 minutes. The wells were washed and phosphotyrosines (PY) were probed with an anti-phosphotyrosine (PY), mAb clone 4G10 (Upstate Biotechnology, Lake Placid, N.Y.). PY/anti-PY complexes were detected with an anti-mouse IgG/HRP conjugate Iamersham International plc, Buckinghamshire, England). Phosphotyrosine was quantitated by incubating with 100 μl 3,3',5,5' tetramethylbenzidine solution (Kirkegaard and Perry, T M B Microwell 1 Component peroxidase substrate). Color development was arrested by the addition of 100 μl 1% HCl-based stop solution (Kirkegaard and Perry, T M B 1 Component Stop Solution).

Optical densities were determined spectrophotometrically at 450 nm in a 96-well plate reader, SpectraMax 250 (Molecular Devices). Background (no ATP in assay) OD values were subtracted from all Ods and the percent inhibition was calculated according to the equation:

$$\% \text{ Inhibition} = \frac{(OD(\text{vehicle control}) - OD(\text{with compound}) \times 100}{OD(\text{vehicle control}) - OD(\text{no } ATP \text{ added})}$$

The $IC_{50}$ values were determined with a least squares analysis program using compound concentration versus percent inhibition.

The following compounds were tested in the assay described above and were found to have either an $IC_{50}$ of less than 10 micromolar or showed greater than 30% inhibition at 1 micromolar. Compound names were generated using Nomenclator™ v 3.0 and may differ from those in the patent applications.

From WO 1999/32463:

| Entry No | Name |
|---|---|
| 73 | N-[5-(tert-butyl)-2-(3-thienyl)phenyl][(4-(4-pyridyloxy)phenyl)amino]carboxamide |
| 96 | {[4-(4-methoxyphenoxy)phenyl]amino}-N-[2-methoxy-5-(trifluoromethyl)phenyl]carboxamide |
| 99 | N-[2-methoxy-5-(trifluoromethyl)phenyl][(3-(4-pyridylthio)phenyl)amino]carboxamide |
| 100 | N-[2-methoxy-5-(trifluoromethyl)phenyl][(3-(4-pyridylthio)phenyl)amino]carboxamide |
| 101 | N-[2-methoxy-5-(trifluoromethyl)phenyl][(4-(4-pyridyloxy)phenyl)amino]carboxamide |
| 11 | N-[5-(tert-butyl)-2-methoxyphenyl][(3-(4-pyridylthio)phenyl)amino]carboxamide |
| 12 | N-[5-(tert-butyl)-2-(3-thienyl)phenyl][(4-(4-pyridyloxy)phenyl)amino]carboxamide |
| 17 | N-[3-(tert-butyl)phenyl][(4-(4-pyridyloxy)phenyl)amino]carboxamide |
| 23 | {[3-(tert-butyl)phenyl]amino}-N-(4-(3-pyridyl)phenyl)carboxamide |
| 33 | {[4-(4-methoxyphenoxy)phenyl]amino}-N-[2-methoxy-5-(trifluoromethyl)phenyl]carboxamide |
| 36 | N-[2-methoxy-5-(trifluoromethyl)phenyl][(3-(4-pyridylthio)phenyl)amino]carboxamide |
| 37 | N-[2-methoxy-5-(trifluoromethyl)phenyl][(3-(4-pyridylthio)phenyl)amino]carboxamide |
| 38 | N-[2-methoxy-5-(trifluoromethyl)phenyl][(4-(4-pyridyloxy)phenyl)amino]carboxamide |
| 56 | N-[2-methoxy-5-(trifluoromethyl)phenyl]{[3-(2-methyl(4-pyridyloxy))phenyl]amino}carboxamide |
| 70 | [(3-chloro-4-(6-quinolyloxy)phenyl)amino]-N-[2-methoxy-5-(trifluoromethyl)phenyl]carboxamide |

-continued

| Entry No | Name |
|---|---|
| 81 | [(4-(4-pyridyloxy)phenyl)amino]-N-[3-(trifluoromethyl)phenyl]carboxamide |
| 82 | N-[2-chloro-5-(trifluoromethyl)phenyl][(4-(4-pyridyloxy)phenyl)amino]carboxamide |
| 83 | N-[2-fluoro-5-(trifluoromethyl)phenyl][(4-(4-pyridyloxy)phenyl)amino]carboxamide |
| 91 | {[4-chloro-3-(trifluoromethyl)phenyl]amino}-N-(2-methyl-4-(3-pyridyloxy)phenyl)carboxamide |
| 102 | N-[4-chloro-3-(trifluoromethyl)phenyl][(4-(4-pyridyloxy)phenyl)amino]carboxamide |
| 103 | N-[4-chloro-3-(trifluoromethyl)phenyl]{[4-(4-methoxyphenoxy)phenyl]amino}carboxamide |
| 105 | {[4-chloro-3-(trifluoromethyl)phenyl]amino}-N-[3-(4-pyridylcarbonyl)phenyl]carboxamide |
| 106 | {[4-chloro-3-(trifluoromethyl)phenyl]amino}-N-[3-(2-methyl(4-pyridyloxy))phenyl]carboxamide |
| 119 | N-[4-fluoro-3-(trifluoromethyl)phenyl][(4-(4-pyridyloxy)phenyl)amino]carboxamide |
| 132 | N-[4-chloro-2-methoxy-5-(trifluoromethyl)phenyl][(4-(4-pyridyloxy)phenyl)amino]carboxamide |
| 133 | N-[5-methoxy-3-(trifluoromethyl)phenyl][(4-(4-pyridyloxy)phenyl)amino]carboxamide |
| 135 | [(3-bromo-4-chlorophenyl)amino]-N-(4-(4-pyridyloxy)phenyl)carboxamide |
| 136 | [(4-(4-pyridyloxy)phenyl)amino]-N-[3-(trifluoromethoxy)phenyl]carboxamide |
| 141 | N-[3,5-bis(trifluoromethyl)phenyl][(4-(4-pyridyloxy)phenyl)amino]carboxamide |

From WO 1999/32111:

| Entry No | Name |
|---|---|
| 18 | N-[5-(tert-butyl)isoxazol-3-yl][(4-(4-pyridylthio)phenyl)amino]carboxamide |
| 32 | {[5-(tert-butyl)isoxazol-3-yl]amino}-N-(3-(4-pyridylthio)phenyl)carboxamide |
| 53 | N-[5-(tert-butyl)isoxazol-3-yl][(4-(4-pyridyloxy)phenyl)amino]carboxamide |
| 59 | N-[5-(tert-butyl)isoxazol-3-yl][(4-(3-pyridyloxy)phenyl)amino]carboxamide |
| 67 | {3-[4-({[5-(tert-butyl)isoxazol-3-yl]amino}carbonylamino)phenoxy]phenyl}-N-methylcarboxamide |
| 85 | {[5-(tert-butyl)isoxazol-3-yl]amino}-N-[3-(2-methyl(4-pyridyloxy))phenyl]carboxamide |
| 86 | N-[5-(tert-butyl)isoxazol-3-yl]{[4-(2-methyl(4-pyridyloxy))phenyl]amino}carboxamide |
| 103 | 4-[4-({[5-(tert-butyl)isoxazol-3-yl]amino}carbonylamino)phenoxy]pyridine-2-carboxamide |
| 104 | {[5-(tert-butyl)isoxazol-3-yl]amino}-N-{3-[2-(N-methylcarbamoyl)(4-pyridyloxy)]phenyl}carboxamide |
| 105 | 4-[3-({N-[5-(tert-butyl)isoxazol-3-yl]carbamoyl}amino)phenoxy]pyridine-2-carboxamide |
| 106 | 3-[4-({[5-(tert-butyl)isoxazol-3-yl]amino}carbonylamino)phenoxy]benzamide |
| 143 | N-[3-(methylethyl)isoxazol-5-yl][(4-(4-pyridyloxy)phenyl)amino]carboxamide |
| 146 | N-(3-cyclobutylisoxazol-5-yl)[(4-(4-pyridyloxy)phenyl)amino]carboxamide |
| 147 | N-(3-cyclobutylisoxazol-5-yl)[(4-(6-quinolyloxy)phenyl)amino]carboxamide |
| 162 | {[3-(tert-butyl)isoxazol-5-yl]amino}-N-(3-(4-pyridylthio)phenyl)carboxamide |
| 163 | N-[3-(tert-butyl)isoxazol-5-yl][(4-(4-pyridyloxy)phenyl)amino]carboxamide |
| 164 | N-[3-(tert-butyl)isoxazol-5-yl]{[4-(4-methoxyphenoxy)phenyl]amino}carboxamide |
| 188 | N-[3-(1,1-dimethylpropyl)isoxazol-5-yl][(3-(4-pyridylthio)phenyl)amino]carboxamide |
| 195 | N-[3-(1,1-dimethylpropyl)isoxazol-5-yl][(4-(4-pyridyloxy)phenyl)amino]carboxamide |

-continued

| Entry No | Name |
|---|---|
| 220 | {[3-(tert-butyl)pyrazol-5-yl]amino}-N-(3-(4-pyridylthio)phenyl)carboxamide |
| 221 | N-[3-(tert-butyl)pyrazol-5-yl][(4-(4-pyridylthio)phenyl)amino]carboxamide |
| 222 | {3-[4-({[3-(tert-butyl)pyrazol-5-yl]amino}carbonylamino)phenoxy]phenyl}-N-methylcarboxamide,2,2,2-trifluoroacetic acid |
| 225 | N-[3-(tert-butyl)-1-methylpyrazol-5-yl][(3-(4-pyridylthio)phenyl)amino]carboxamide |
| 251 | N-[3-(tert-butyl)-1-methylpyrazol-5-yl][(4-(4-pyridyloxy)phenyl)amino]carboxamide |
| 261 | N-[3-(tert-butyl)-1-methylpyrazol-5-yl]{[4-(4-pyridylmethyl)phenyl]amino}carboxamide |
| 266 | N-[3-(tert-butyl)-1-methylpyrazol-5-yl]{[4-(4-pyridylmethoxy)phenyl]amino}carboxamide |
| 277 | tert-butyl 3-(tert-butyl)-5-[({4-[3-(N-methylcarbamoyl)phenoxy]phenyl}amino)carbonylamino]pyrazolecarboxylate |
| 280 | N-[5-(tert-butyl)(1,3,4-thiadiazol-2-yl)][(4-(4-pyridyloxy)phenyl)amino]carboxamide |
| 281 | {[5-(tert-butyl)(1,3,4-thiadiazol-2-yl)]amino}-N-(3-(4-pyridylthio)phenyl)carboxamide |
| 284 | N-[5-(tert-butyl)(3-thienyl)][(4-(3-pyridyloxy)phenyl)amino]carboxamide |
| 293 | N-[5-(tert-butyl)(3-thienyl)][(4-(4-pyridyloxy)phenyl)amino]carboxamide |
| 299 | N-(6-chloro(1H-indazol-3-yl))[(4-(4-pyridyloxy)phenyl)amino]carboxamide |
| 302 | ({4-[2-(N-methylcarbamoyl)(4-pyridyloxy)]phenyl}amino)-N-(1-methyl-3-phenylpyrazol-5-yl)carboxamide |

From WO 1999

| Entry No | Name |
|---|---|
| 21 | N-[5-(tert-butyl)isoxazol-3-yl][(4-(4-pyridylthio)phenyl)amino]carboxamide |
| 42 | {[5-(tert-butyl)isoxazol-3-yl]amino}-N-(3-(4-pyridylthio)phenyl)carboxamide |
| 59 | N-[5-(tert-butyl)isoxazol-3-yl][(4-(4-pyridyloxy)phenyl)amino]carboxamide |
| 64 | N-[5-(tert-butyl)isoxazol-3-yl][(4-(3-pyridyloxy)phenyl)amino]carboxamide |
| 69 | {3-[4-({[5-(tert-butyl)isoxazol-3-yl]amino}carbonylamino)phenoxy]phenyl}-N-methylcarboxamide |
| 81 | {[5-(tert-butyl)isoxazol-3-yl]amino}-N-[3-(2-methyl(4-pyridyloxy))phenyl]carboxamide |
| 82 | N-[5-(tert-butyl)isoxazol-3-yl]{[4-(2-methyl(4-pyridyloxy))phenyl]amino}carboxamide |
| 101 | {4-[4-({[5-(tert-butyl)isoxazol-3-yl]amino}carbonylamino)phenoxy](2-pyridyl)}-N-methylcarboxamide |
| 103 | 4-[4-({[5-(tert-butyl)isoxazol-3-yl]amino}carbonylamino)phenoxy]pyridine-2-carboxamide |
| 104 | 4-[3-({N-[5-(tert-butyl)isoxazol-3-yl]carbamoyl}amino)phenoxy]pyridine-2-carboxamide |
| 105 | {[5-(tert-butyl)isoxazol-3-yl]amino}-N-{3-[2-(N-methylcarbamoyl)(4-pyridyloxy)]phenyl}carboxamide |
| 106 | 3-[4-({[5-(tert-butyl)isoxazol-3-yl]amino}carbonylamino)phenoxy]benzamide |
| 118 | {4-[4-({[5-(tert-butyl)isoxazol-3-yl]amino}carbonylamino)-3-chlorophenoxy](2-pyridyl)}-N-methylcarboxamide |
| 124 | {3-[4-({[5-(tert-butyl)isoxazol-3-yl]amino}carbonylamino)phenoxy]phenyl}-N-(2-morpholin-4-ylethyl)carboxamide |
| 125 | {4-[4-({[5-(tert-butyl)isoxazol-3-yl]amino}carbonylamino)phenoxy](2-pyridyl)}-N-ethylcarboxamide |
| 126 | {4-[4-({[5-(tert-butyl)isoxazol-3-yl]amino}carbonylamino)-2-chlorophenoxy](2-pyridyl)}-N-methylcarboxamide |
| 127 | {[5-(tert-butyl)isoxazol-3-yl]amino}-N-{2-methyl-4-[2-(N-methylcarbamoyl)(4-pyridyloxy)]phenyl}carboxamide |
| 128 | {[5-(tert-butyl)isoxazol-3-yl]amino}-N-{3-[2-(N-methylcarbamoyl)(4-pyridylthio)]phenyl}carboxamide |

-continued

| Entry No | Name |
|---|---|
| 130 | {3-[4-({[5-(tert-butyl)isoxazol-3-yl]amino}carbonylamino)phenoxy]phenyl}-N-(3-pyridyl)carboxamide |
| 140 | {4-[4-({[5-(tert-butyl)isoxazol-3-yl]amino}carbonylamino)phenylthio](2-pyridyl)}-N-methylcarboxamide |
| 182 | N-methyl{4-[4-({[3-(methylethyl)isoxazol-5-yl]amino}carbonylamino)phenoxy](2-pyridyl)}carboxamide |
| 186 | N-methyl{4-[3-({[3-(methylethyl)isoxazol-5-yl]amino}carbonylamino)phenoxy](2-pyridyl)}carboxamide |
| 187 | N-(3-cyclobutylisoxazol-5-yl)[(4-(6-quinolyloxy)phenyl)amino]carboxamide |
| 188 | N-(3-cyclobutylisoxazol-5-yl)[(4-(4-pyridyloxy)phenyl)amino]carboxamide |
| 194 | N-[3-(tert-butyl)isoxazol-5-yl][(4-(4-pyridyloxy)phenyl)amino]carboxamide |
| 195 | N-[3-(tert-butyl)isoxazol-5-yl]{[4-(4-methoxyphenoxy)phenyl]amino}carboxamide |
| 206 | {[3-(tert-butyl)isoxazol-5-yl]amino}-N-(3-(4-pyridylthio)phenyl)carboxamide |
| 212 | N-[3-(tert-butyl)isoxazol-5-yl]{[4-(1,3-dioxoisoindolin-5-yloxy)phenyl]amino}carboxamide |
| 213 | {[3-(tert-butyl)isoxazol-5-yl]amino}-N-[4-(1-oxoisoindolin-5-yloxy)phenyl]carboxamide |
| 214 | {4-[4-({[3-(tert-butyl)isoxazol-5-yl]amino}carbonylamino)phenoxy](2-pyridyl)}-N-ethylcarboxamide |
| 215 | {4-[4-({[3-(tert-butyl)isoxazol-5-yl]amino}carbonylamino)-2-chlorophenoxy](2-pyridyl)}-N-methylcarboxamide |
| 216 | {[3-(tert-butyl)isoxazol-5-yl]amino}-N-{3-[2-(N-methylcarbamoyl)(4-pyridylthio)]phenyl}carboxamide |
| 217 | {4-[4-({[3-(tert-butyl)isoxazol-5-yl]amino}carbonylamino)phenylthio](2-pyridyl)}-N-methylcarboxamide |
| 218 | {4-[4-({[3-(tert-butyl)isoxazol-5-yl]amino}carbonylamino)phenoxy](2-pyridyl)}-N-methylcarboxamide |
| 228 | {[3-(tert-butyl)isoxazol-5-yl]amino}-N-[3-(6-methyl(3-pyridyloxy))phenyl]carboxamide |
| 240 | N-[3-(tert-butyl)isoxazol-5-yl][(6-(4-pyridylthio)(3-pyridyl))amino]carboxamide |
| 247 | {[3-(tert-butyl)isoxazol-5-yl]amino}-N-{3-[2-(N-methylcarbamoyl)(4-pyridyloxy)]phenyl}carboxamide |
| 253 | N-[3-(1,1-dimethylpropyl)isoxazol-5-yl][(3-(4-pyridylthio)phenyl)amino]carboxamide |
| 255 | N-[3-(1,1-dimethylpropyl)isoxazol-5-yl][(4-(4-pyridyloxy)phenyl)amino]carboxamide |
| 261 | N-[3-(1,1-dimethylpropyl)isoxazol-5-yl]({4-[2-(N-methylcarbamoyl)(4-pyridyloxy)]phenyl}amino)carboxamide |
| 263 | N-[3-(1,1-dimethylpropyl)isoxazol-5-yl]{[4-(2-methyl(4-pyridylthio))phenyl]amino}carboxamide |
| 292 | N-[3-(tert-butyl)pyrazol-5-yl]{[4-(6-methyl(3-pyridyloxy))phenyl]amino}carboxamide |
| 298 | {[3-(tert-butyl)pyrazol-5-yl]amino}-N-(3-(4-pyridylthio)phenyl)carboxamide |
| 299 | N-[3-(tert-butyl)pyrazol-5-yl][(4-(4-pyridylthio)phenyl)amino]carboxamide |
| 300 | {3-[4-({[3-(tert-butyl)pyrazol-5-yl]amino}carbonylamino)phenoxy]phenyl}-N-methylcarboxamide, 2,2,2-trifluoroacetic acid |
| 304 | N-[3-(tert-butyl)-1-methylpyrazol-5-yl]{[4-(4-pyridylmethoxy)phenyl]amino}carboxamide |
| 305 | {5-[4-({[3-(tert-butyl)-1-methylpyrazol-5-yl]amino}carbonylamino)phenoxy]-2-methoxyphenyl}-N-methylcarboxamide |
| 309 | N-[3-(tert-butyl)-1-methylpyrazol-5-yl][(3-(4-pyridylthio)phenyl)amino]carboxamide |
| 321 | N-[3-(tert-butyl)-1-methylpyrazol-5-yl][(4-(4-pyridyloxy)phenyl)amino]carboxamide |
| 326 | N-[3-(tert-butyl)-1-methylpyrazol-5-yl]{[4-(4-pyridylmethyl)phenyl]amino}carboxamide |
| 339 | tert-butyl 3-(tert-butyl)-5-[({4-[3-(N-methylcarbamoyl)phenoxy]phenyl}amino)carbonylamino]pyrazolecarboxylate |
| 341 | N-[5-(tert-butyl)(1,3,4-thiadiazol-2-yl)][(4-(4-pyridyloxy)phenyl)amino]carboxamide |
| 342 | {[5-(tert-butyl)(1,3,4-thiadiazol-2-yl)]amino}-N-(3-(4-pyridylthio)phenyl)carboxamide |

| Entry No | Name |
|---|---|
| 356 | N-[5-(tert-butyl)(1,3,4-thiadiazol-2-yl)]{[6-(6-methyl(3-pyridyloxy))(3-pyridyl)]amino}carboxamide |
| 366 | N-[5-(1,1-dimethylpropyl)(1,3,4-thiadiazol-2-yl)][(4-(4-pyridyloxy)phenyl]amino]carboxamide |
| 367 | N-[5-(1,1-dimethylpropyl)(1,3,4-thiadiazol-2-yl)][(3-(4-pyridylthio)phenyl]amino]carboxamide |
| 376 | N-[5-(tert-butyl)(3-thienyl)][(4-(3-pyridyloxy)phenyl)amino]carboxamide |
| 388 | {3-[4-({[5-(tert-butyl)(1,3,4-oxadiazol-2-yl)]amino}carbonylamino)phenoxy]phenyl}-N-ethylcarboxamide |
| 389 | {3-[4-({[5-(tert-butyl)(1,3,4-oxadiazol-2-yl)]amino}carbonylamino)phenoxy]phenyl}-N-(methylethyl)carboxamide |
| 390 | {3-[4-({[5-(tert-butyl)(1,3,4-oxadiazol-2-yl)]amino}carbonylamino)phenoxy]phenyl}-N-methylcarboxamide |
| 391 | N-[5-(tert-butyl)(1,3,4-oxadiazol-2-yl)][(4-(4-pyridyloxy)phenyl]amino]carboxamide |
| 392 | N-(3-cyclopropyl-1-methylpyrazol-5-yl)[(4-(6-quinolyloxy)phenyl)amino]carboxamide |
| 393 | ({4-[2-(N-methylcarbamoyl)(4-pyridyloxy)]phenyl}amino)-N-(1-methyl-3-phenylpyrazol-5-yl)carboxamide |
| 395 | N-[2-(tert-butyl)(1,3-thiazol-5-yl)]{[4-(6-methyl(3-pyridyloxy))phenyl]amino}carboxamide |

From WO 1999/32110

| Entry No | Name |
|---|---|
| 1 | [(2,3-dichlorophenyl)amino]-N-[3-(tert-butyl)-1-phenylpyrazol-5-yl]carboxamide |
| 2 | N-[1-(4-aminophenyl)-3-(tert-butyl)pyrazol-5-yl][(2,3-dichlorophenyl)amino]carboxamide |
| 11 | N-[1-(3-aminophenyl)-3-(tert-butyl)pyrazol-5-yl][(2,3-dichlorophenyl)amino]carboxamide |
| 18 | N-[3-(3-(tert-butyl)-5-{[(4-phenoxyphenyl)amino]carbonylamino}pyrazolyl)phenyl]acetamide |
| 23 | N-[1-(2,6-dichlorophenyl)-3-(tert-butyl)pyrazol-5-yl]{[4-(4-pyridylmethyl)phenyl]amino}carboxamide |
| 24 | N-[3-(tert-butyl)-1-(4-fluorophenyl)pyrazol-5-yl]{[4-(4-pyridylmethyl)phenyl]amino}carboxamide |
| 25 | N-[3-(tert-butyl)-1-(2-methylphenyl)pyrazol-5-yl]{[4-(4-pyridylmethyl)phenyl]amino}carboxamide |
| 26 | N-[3-(tert-butyl)-1-(3-fluorophenyl)pyrazol-5-yl]{[4-(4-pyridylmethyl)phenyl]amino}carboxamide |
| 27 | N-{3-(tert-butyl)-1-[4-(methylsulfonyl)phenyl]pyrazol-5-yl}{[4-(4-pyridylmethyl)phenyl]amino}carboxamide |
| 28 | N-[3-(tert-butyl)-1-(4-nitrophenyl)pyrazol-5-yl]{[4-(4-pyridylmethyl)phenyl]amino}carboxamide |
| 29 | N-[3-(tert-butyl)-1-(3-methoxyphenyl)pyrazol-5-yl]{[4-(4-pyridylmethyl)phenyl]amino}carboxamide |
| 30 | N-[1-(3-aminophenyl)-3-(tert-butyl)pyrazol-5-yl]{[4-(4-pyridylmethyl)phenyl]amino}carboxamide |
| 32 | N-[1-(3-aminophenyl)-3-(tert-butyl)pyrazol-5-yl][(4-(4-pyridylthio)phenyl]amino]carboxamide |
| 34 | N-[3-(tert-butyl)-1-(3-fluorophenyl)pyrazol-5-yl][(3-(4-pyridylthio)phenyl]amino]carboxamide |
| 35 | N-[3-(tert-butyl)-1-(4-fluorophenyl)pyrazol-5-yl][(3-(4-pyridylthio)phenyl]amino]carboxamide |
| 36 | N-[3-(tert-butyl)-1-(3-fluorophenyl)pyrazol-5-yl][(4-(4-pyridyloxy)phenyl]amino]carboxamide |
| 37 | N-[3-(tert-butyl)-1-(4-fluorophenyl)pyrazol-5-yl][(4-(4-pyridyloxy)phenyl]amino]carboxamide |

From WO 1999/32455

| Entry No | Name |
|---|---|
| 1 | [(2,3-dichlorophenyl)amino]-N-[3-(tert-butyl)-1-phenylpyrazol-5-yl]carboxamide |
| 2 | N-[1-(4-aminophenyl)-3-(tert-butyl)pyrazol-5-yl][(2,3-dichlorophenyl)amino]carboxamide |
| 14 | N-[1-(3-aminophenyl)-3-(tert-butyl)pyrazol-5-yl][(2,3-dichlorophenyl)amino]carboxamide |
| 22 | N-[3-(3-(tert-butyl)-5-{[(4-phenoxyphenyl)amino]carbonylamino}pyrazolyl)phenyl]acetamide |
| 27 | N-[1-(2,6-dichlorophenyl)-3-(tert-butyl)pyrazol-5-yl]{[4-(4-pyridylmethyl)phenyl]amino}carboxamide |
| 28 | N-[3-(tert-butyl)-1-(4-fluorophenyl)pyrazol-5-yl]{[4-(4-pyridylmethyl)phenyl]amino}carboxamide |
| 29 | N-[3-(tert-butyl)-1-(2-methylphenyl)pyrazol-5-yl]{[4-(4-pyridylmethyl)phenyl]amino}carboxamide |
| 30 | N-[3-(tert-butyl)-1-(3-fluorophenyl)pyrazol-5-yl]{[4-(4-pyridylmethyl)phenyl]amino}carboxamide |
| 31 | N-{3-(tert-butyl)-1-[4-(methylsulfonyl)phenyl]pyrazol-5-yl}{[4-(4-pyridylmethyl)phenyl]amino}carboxamide |
| 32 | N-[3-(tert-butyl)-1-(4-nitrophenyl)pyrazol-5-yl]{[4-(4-pyridylmethyl)phenyl]amino}carboxamide |
| 33 | N-[3-(tert-butyl)-1-(3-methoxyphenyl)pyrazol-5-yl]{[4-(4-pyridylmethyl)phenyl]amino}carboxamide |
| 34 | N-[1-(3-aminophenyl)-3-(tert-butyl)pyrazol-5-yl]{[4-(4-pyridylmethyl)phenyl]amino}carboxamide |
| 36 | N-[1-(3-aminophenyl)-3-(tert-butyl)pyrazol-5-yl][(4-(4-pyridylthio)phenyl]amino]carboxamide |

From WO 2000/41698

| Entry No | Name |
|---|---|
| 1 | {3-[4-({[3-(tert-butyl)phenyl]amino}carbonylamino)phenoxy]phenyl}-N-methylcarboxamide |
| 11 | N-[2-methoxy-5-(trifluoromethyl)phenyl]({3-[2-(N-methylcarbamoyl)(4-pyridyloxy)]phenyl}amino)carboxamide |
| 12 | 4-[3-({N-[2-methoxy-5-(trifluoromethyl)phenyl]carbamoyl}amino)phenoxy]pyridine-2-carboxamide |

| Entry No | Name |
|---|---|
| 13 | N-[2-methoxy-5-(trifluoromethyl)phenyl]({4-[2-(N-methylcarbamoyl)(4-pyridyloxy)]phenyl}amino)carboxamide |
| 14 | 4-[4-({N-[2-methoxy-5-(trifluoromethyl)phenyl]carbamoyl}amino)phenoxy]pyridine-2-carboxamide |
| 16 | {4-[4-({N-[2-methoxy-5-(trifluoromethyl)phenyl]carbamoyl}amino)-3-methylphenoxy](2-pyridyl)}-N-methylcarboxamide |
| 17 | ({2-chloro-4-[2-(N-methylcarbamoyl)(4-pyridyloxy)]phenyl}amino)-N-[2-methoxy-5-(trifluoromethyl)phenyl]carboxamide |
| 19 | ({4-[2-(N-ethylcarbamoyl)(4-pyridyloxy)]phenyl}amino)-N-[2-methoxy-5-(trifluoromethyl)phenyl]carboxamide |
| 20 | ({3-chloro-4-[2-(N-methylcarbamoyl)(4-pyridyloxy)]phenyl}amino)-N-[2-methoxy-5-(trifluoromethyl)phenyl]carboxamide |
| 22 | 3-[4-({N-[2-methoxy-5-(trifluoromethyl)phenyl]carbamoyl}amino)phenoxy]benzamide |
| 24 | ({4-[2-(N,N-dimethylcarbamoyl)(4-pyridyloxy)]phenyl}amino)-N-[2-methoxy-5-(trifluoromethyl)phenyl]carboxamide |
| 27 | N-[2-methoxy-5-(trifluoromethyl)phenyl]({4-[2-(N-methylcarbamoyl)(4-pyridylthio)]phenyl}amino)carboxamide |
| 29 | N-[2-methoxy-5-(trifluoromethyl)phenyl]({3-[2-(N-methylcarbamoyl)(4-pyridylthio)]phenyl}amino)carboxamide |
| 31 | N-[2-methoxy-5-(trifluoromethyl)phenyl][(4-{5-[N-(2-morpholin-4-ylethyl)carbamoyl](3-pyridyloxy)}phenyl)amino]carboxamide |
| 32 | N-[2-methoxy-5-(trifluoromethyl)phenyl]({4-[5-(N-methylcarbamoyl)(3-pyridyloxy)]phenyl}amino)carboxamide |
| 34 | N-[2-methoxy-5-(trifluoromethyl)phenyl]({4-[3-(N-(3-pyridyl)carbamoyl)phenoxy]phenyl}amino)carboxamide |
| 42 | {4-[4-({[4-chloro-3-(trifluoromethyl)phenyl]amino}carbonylamino)phenoxy](2-pyridyl)}-N-methylcarboxamide |
| 43 | 4-[4-({[4-chloro-3-(trifluoromethyl)phenyl]amino}carbonylamino)phenoxy]pyridine-2-carboxamide |
| 44 | 4-[3-({[4-chloro-3-(trifluoromethyl)phenyl]amino}carbonylamino)phenoxy]pyridine-2-carboxamide |
| 45 | {[4-chloro-3-(trifluoromethyl)phenyl]amino}-N-{3-[2-(N-methylcarbamoyl)(4-pyridyloxy)]phenyl}carboxamide |
| 47 | {[4-chloro-3-(trifluoromethyl)phenyl]amino}-N-{2-methyl-4-[2-(N-methylcarbamoyl)(4-pyridyloxy)]phenyl}carboxamide |
| 49 | {4-[3-chloro-4-({[4-chloro-3-(trifluoromethyl)phenyl]amino}carbonylamino)phenoxy](2-pyridyl)}-N-methylcarboxamide |
| 51 | N-[4-chloro-3-(trifluoromethyl)phenyl]({4-[2-(N-ethylcarbamoyl)(4-pyridyloxy)]phenyl}amino)carboxamide |
| 61 | {3-[4-({[4-chloro-3-(trifluoromethyl)phenyl]amino}carbonylamino)phenoxy]phenyl}-N-(2-morpholin-4-ylethyl)carboxamide |
| 62 | {3-[4-({[4-chloro-3-(trifluoromethyl)phenyl]amino}carbonylamino)phenoxy]phenyl}-N-(2-piperidylethyl)carboxamide |
| 65 | {4-[4-({[4-chloro-3-(trifluoromethyl)phenyl]amino}carbonylamino)phenylthio](2-pyridyl)}-N-methylcarboxamide |
| 69 | {[4-chloro-3-(trifluoromethyl)phenyl]amino}-N-{3-[2-(N-methylcarbamoyl)(4-pyridylthio)]phenyl}carboxamide |
| 70 | {4-[4-({[4-chloro-3-(trifluoromethyl)phenyl]amino}carbonylamino)phenoxy](2-pyridyl)}-N-(2-morpholin-4-ylethyl)carboxamide |
| 72 | {5-[4-({[4-chloro-3-(trifluoromethyl)phenyl]amino}carbonylamino)phenoxy](3-pyridyl)}-N-methylcarboxamide |
| 75 | N-[4-chloro-3-(trifluoromethyl)phenyl]({4-[3-(N-(3-pyridyl)carbamoyl)phenoxy]phenyl}amino)carboxamide |
| 84 | {4-[4-({[4-chloro-3-(trifluoromethyl)phenyl]amino}carbonylamino)phenoxy](2-pyridyl)}-N-(2-hydroxyethyl)carboxamide |
| 87 | {4-[4-({[4-bromo-3-(trifluoromethyl)phenyl]amino}carbonylamino)-2-chlorophenoxy](2-pyridyl)}-N-methylcarboxamide |
| 88 | N-[4-bromo-3-(trifluoromethyl)phenyl]({4-[2-(N-ethylcarbamoyl)(4-pyridyloxy)]phenyl}amino)carboxamide |
| 89 | {[4-bromo-3-(trifluoromethyl)phenyl]amino}-N-{3-[2-(N-methylcarbamoyl)(4-pyridyloxy)]phenyl}carboxamide |
| 90 | {[4-bromo-3-(trifluoromethyl)phenyl]amino}-N-{4-methyl-3-[2-(N-methylcarbamoyl)(4-pyridyloxy)]phenyl}carboxamide |
| 93 | {[4-bromo-3-(trifluoromethyl)phenyl]amino}-N-{3-[2-(N-methylcarbamoyl)(4-pyridylthio)]phenyl}carboxamide |
| 94 | {4-[4-({[4-bromo-3-(trifluoromethyl)phenyl]amino}carbonylamino)phenoxy](2-pyridyl)}-N-(2-morpholin-4-ylethyl)carboxamide |
| 95 | N-[4-chloro-2-methoxy-5-(trifluoromethyl)phenyl]({4-[2-(N-methylcarbamoyl)(4-pyridyloxy)]phenyl}amino)carboxamide |
| 96 | N-[4-chloro-2-methoxy-5-(trifluoromethyl)phenyl]({2-chloro-4-[2-(N-methylcarbamoyl)(4-pyridyloxy)]phenyl}amino)carboxamide |
| 97 | N-[4-chloro-2-methoxy-5-(trifluoromethyl)phenyl]({3-chloro-4-[2-(N-methylcarbamoyl)(4-pyridyloxy)]phenyl}amino)carboxamide |
| 98 | N-[4-chloro-2-methoxy-5-(trifluoromethyl)phenyl]({3-[2-(N-methylcarbamoyl)(4-pyridyloxy)]phenyl}amino)carboxamide |
| 99 | N-[4-chloro-2-methoxy-5-(trifluoromethyl)phenyl]({4-[2-(N-ethylcarbamoyl)(4-pyridyloxy)]phenyl}amino)carboxamide |

From WO 2000/42012

| Entry No | Name |
|---|---|
| 1 | {3-[4-({[3-(tert-butyl)phenyl]amino}carbonylamino)phenoxy]phenyl}-N-methylcarboxamide |
| 11 | N-[2-methoxy-5-(trifluoromethyl)phenyl]({3-[2-(N-methylcarbamoyl)(4-pyridyloxy)]phenyl}amino)carboxamide |
| 12 | 4-[3-({N-[2-methoxy-5-(trifluoromethyl)phenyl]carbamoyl}amino)phenoxy]pyridine-2-carboxamide |
| 13 | N-[2-methoxy-5-(trifluoromethyl)phenyl]({4-[2-(N-methylcarbamoyl)(4-pyridyloxy)]phenyl}amino)carboxamide |
| 14 | 4-[4-({N-[2-methoxy-5-(trifluoromethyl)phenyl]carbamoyl}amino)phenoxy]pyridine-2-carboxamide |
| 16 | {4-[4-({N-[2-methoxy-5-(trifluoromethyl)phenyl]carbamoyl}amino)-3-methylphenoxy](2-pyridyl)}-N-methylcarboxamide |
| 17 | ({2-chloro-4-[2-(N-methylcarbamoyl)(4-pyridyloxy)]phenyl}amino)-N-[2-methoxy-5-(trifluoromethyl)phenyl]carboxamide |
| 19 | ({4-[2-(N-ethylcarbamoyl)(4-pyridyloxy)]phenyl}amino)-N-[2-methoxy-5-(trifluoromethyl)phenyl]carboxamide |
| 20 | ({3-chloro-4-[2-(N-methylcarbamoyl)(4-pyridyloxy)]phenyl}amino)-N-[2-methoxy-5-(trifluoromethyl)phenyl]carboxamide |
| 22 | 3-[4-({N-[2-methoxy-5-(trifluoromethyl)phenyl]carbamoyl}amino)phenoxy]benzamide |
| 24 | ({4-[2-(N,N-dimethylcarbamoyl)(4-pyridyloxy)]phenyl}amino)-N-[2-methoxy-5-(trifluoromethyl)phenyl]carboxamide |
| 27 | N-[2-methoxy-5-(trifluoromethyl)phenyl]({4-[2-(N-methylcarbamoyl)(4-pyridylthio)]phenyl}amino)carboxamide |
| 29 | N-[2-methoxy-5-(trifluoromethyl)phenyl]({3-[2-(N-methylcarbamoyl)(4-pyridylthio)]phenyl}amino)carboxamide |
| 31 | N-[2-methoxy-5-(trifluoromethyl)phenyl][(4-{5-[N-(2-morpholin-4-ylethyl)carbamoyl](3-pyridyloxy)}phenyl)amino]carboxamide |
| 32 | N-[2-methoxy-5-(trifluoromethyl)phenyl]({4-[5-(N-methylcarbamoyl)(3-pyridyloxy)]phenyl}amino)carboxamide |
| 34 | N-[2-methoxy-5-(trifluoromethyl)phenyl]({4-[3-(N-(3-pyridyl)carbamoyl)phenoxy]phenyl}amino)carboxamide |
| 42 | {4-[4-({[4-chloro-3-(trifluoromethyl)phenyl]amino}carbonylamino)phenoxy](2-pyridyl)}-N-methylcarboxamide |
| 43 | 4-[4-({[4-chloro-3-(trifluoromethyl)phenyl]amino}carbonylamino)phenoxy]pyridine-2-carboxamide |

-continued

| Entry No | Name |
|---|---|
| 44 | 4-[3-({[4-chloro-3-(trifluoromethyl)phenyl]amino}carbonylamino)phenoxy]pyridine-2-carboxamide |
| 45 | {[4-chloro-3-(trifluoromethyl)phenyl]amino}-N-{3-[2-(N-methylcarbamoyl)(4-pyridyloxy)]phenyl}carboxamide |
| 47 | {[4-chloro-3-(trifluoromethyl)phenyl]amino}-N-{2-methyl-4-[2-(N-methylcarbamoyl)(4-pyridyloxy)]phenyl}carboxamide |
| 49 | {4-[3-chloro-4-({[4-chloro-3-(trifluoromethyl)phenyl]amino}carbonylamino)phenoxy](2-pyridyl)}-N-methylcarboxamide |
| 51 | N-[4-chloro-3-(trifluoromethyl)phenyl]({4-[2-(N-ethylcarbamoyl)(4-pyridyloxy)]phenyl}amino)carboxamide |
| 61 | {3-[4-({[4-chloro-3-(trifluoromethyl)phenyl]amino}carbonylamino)phenoxy]phenyl}-N-(2-morpholin-4-ylethyl)carboxamide |
| 62 | {3-[4-({[4-chloro-3-(trifluoromethyl)phenyl]amino}carbonylamino)phenoxy]phenyl}-N-(2-piperidylethyl)carboxamide |
| 65 | {4-[4-({[4-chloro-3-(trifluoromethyl)phenyl]amino}carbonylamino)phenylthio](2-pyridyl)}-N-methylcarboxamide |
| 69 | {[4-chloro-3-(trifluoromethyl)phenyl]amino}-N-{3-[2-(N-methylcarbamoyl)(4-pyridylthio)]phenyl}carboxamide |
| 70 | {4-[4-({[4-chloro-3-(trifluoromethyl)phenyl]amino}carbonylamino)phenoxy](2-pyridyl)}-N-(2-morpholin-4-ylethyl)carboxamide |
| 72 | {5-[4-({[4-chloro-3-(trifluoromethyl)phenyl]amino}carbonylamino)phenoxy](3-pyridyl)}-N-methylcarboxamide |
| 75 | N-[4-chloro-3-(trifluoromethyl)phenyl]({4-[3-(N-(3-pyridyl)carbamoyl)phenoxy]phenyl}amino)carboxamide |
| 84 | {4-[4-({[4-chloro-3-(trifluoromethyl)phenyl]amino}carbonylamino)phenoxy](2-pyridyl)}-N-(2-hydroxyethyl)carboxamide |
| 87 | {4-[4-({[4-bromo-3-(trifluoromethyl)phenyl]amino}carbonylamino)-2-chlorophenoxy](2-pyridyl)}-N-methylcarboxamide |
| 88 | N-[4-bromo-3-(trifluoromethyl)phenyl]({4-[2-(N-ethylcarbamoyl)(4-pyridyloxy)]phenyl}amino)carboxamide |
| 89 | {[4-bromo-3-(trifluoromethyl)phenyl]amino}-N-{3-[2-(N-methylcarbamoyl)(4-pyridyloxy)]phenyl}carboxamide |
| 90 | {[4-bromo-3-(trifluoromethyl)phenyl]amino}-N-{4-methyl-3-[2-(N-methylcarbamoyl)(4-pyridyloxy)]phenyl}carboxamide |
| 93 | {[4-bromo-3-(trifluoromethyl)phenyl]amino}-N-{3-[2-(N-methylcarbamoyl)(4-pyridylthio)]phenyl}carboxamide |
| 94 | {4-[4-({[4-bromo-3-(trifluoromethyl)phenyl]amino}carbonylamino)phenoxy](2-pyridyl)}-N-(2-morpholin-4-ylethyl)carboxamide |
| 95 | N-[4-chloro-2-methoxy-5-(trifluoromethyl)phenyl]({4-[2-(N-methylcarbamoyl)(4-pyridyloxy)]phenyl}amino)carboxamide |
| 96 | N-[4-chloro-2-methoxy-5-(trifluoromethyl)phenyl]({2-chloro-4-[2-(N-methylcarbamoyl)(4-pyridyloxy)]phenyl}amino)carboxamide |
| 97 | N-[4-chloro-2-methoxy-5-(trifluoromethyl)phenyl]({3-chloro-4-[2-(N-methylcarbamoyl)(4-pyridyloxy)]phenyl}amino)carboxamide |
| 98 | N-[4-chloro-2-methoxy-5-(trifluoromethyl)phenyl]({3-[2-(N-methylcarbamoyl)(4-pyridyloxy)]phenyl}amino)carboxamide |
| 99 | N-[4-chloro-2-methoxy-5-(trifluoromethyl)phenyl]({4-[2-(N-ethylcarbamoyl)(4-pyridyloxy)]phenyl}amino)carboxamide |

From WO 2002/85859

| Entry No | Name |
|---|---|
| 16 | [(4-fluorophenyl)amino]-N-(3-isoquinolyl)carboxamide |
| 25 | N-(2-methoxy(3-quinolyl))[(4-(4-pyridyloxy)phenyl)amino]carboxamide |
| 27 | N-(2-methoxy(3-quinolyl))[(3-(4-pyridylthio)phenyl)amino]carboxamide |
| 28 | N-[1-(4-methylpiperazinyl)(3-isoquinolyl)][(4-(4-pyridyloxy)phenyl)amino]carboxamide |

From WO 2002/85857

| Entry No | Name |
|---|---|
| 25 | N-(2-methoxy(3-quinolyl))[(4-(4-pyridyloxy)phenyl)amino]carboxamide |
| 27 | N-(2-methoxy(3-quinolyl))[(3-(4-pyridylthio)phenyl)amino]carboxamide |
| 28 | N-[1-(4-methylpiperazinyl)(3-isoquinolyl)][(4-(4-pyridyloxy)phenyl)amino]carboxamide |

Cell Mechanistic Assay-Inhibition of 3T3 KDR Phosphorylation:

NIH3T3 cells expressing the full length KDR receptor are grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ml of G418 (Life Technologies Inc., Grand Island, N.Y.). The cells are maintained in collagen I-coated T75 flasks (Becton Dickinson Labware, Bedford, Mass.) in a humidified 5% CO2 atmosphere at 37° C.

Fifteen thousand cells are plated into each well of a collagen I-coated 96-well plate in the DMEM growth medium. Six hours later, the cells are washed and the medium is replaced with DMEM without serum. After overnight culture to quiesce the cells, the medium is replaced by Dulbecco's phosphate-buffered saline (Life Technologies Inc., Grand Island, N.Y.) with 0.1% bovine albumin (Sigma Chemical Co., St. Louis, Mo.). After adding various concentrations (0-300 nM) of test compounds to the cells in 1% final concentration of DMSO, the cells are incubated at room temperature for 30 minutes. Following VEGF stimulation, the buffer is removed and the cells are lysed by addition of 150 µl of extraction buffer (50 mM Tris, pH 7.8, supplemented with 10% glycerol, 50 mM BGP, 2 mM EDTA, 10 mM NaF, 0.5 mM NaVO4, and 0.3% TX-100) at 4° C. for 30 minutes.

To assess receptor phosphorylation, 100 microliters of each cell lysate are added to the wells of an ELISA plate precoated with 300 ng of antibody C20 (Santa Cruz Biotechnology, Inc., Santa Cruz, Calif.). Following a 60-minute incubation, the plate is washed and bound KDR is probed for phosphotyrosine using an anti-phosphotyrosine mAb clone 4010 (Upstate Biotechnology, Lake Placid, N.Y.). The plate is washed and wells are incubated with anti-mouse IgG/HRP conjugate (Amersham International plc, Buckinghamshire, England) for 60 minutes. Wells are washed and phosphotyrosine is quantitated by addition of 100 µl per well of 3,3',5,5' tetramethylbenzidine (Kirkegaard and Perry, T M B 1 Component Stop Solution).

Optical densities (OD) are determined spectrophotometrically at 450 mm in a 96-well plate reader (SpectraMax 250, Molecular Devices). Background (no VEGF added) OD values are subtracted from all Ods and percent inhibition is calculated according to the equation:

$$\% \text{ Inhibition} = \frac{(OD(VEGF \text{ control}) - OD(\text{with test compound}) \times 100}{OD(VEGF \text{ control}) - OD(\text{no } VEGF \text{ added})}$$

$IC_{50S}$ are determined on some of the exemplary materials with at least squares analysis program using compound concentration versus percent inhibition.

Matrigel® Anaiogenesis Model:

Preparation of Martigel Plugs and in vivo Phase: Matrigel® (Collaborative Biomedical Products, Bedord, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. is mixed with SK-MEL2 human tumor cells that are transfected with a plasmid containing the murine VEGF gene with a selectable marker. Tumor cells are grown in vitro under selection and cells are mixed with cold liquid Matrigel at a ratio of $2 \times 10^6$ per 0.5 ml. One half milliliter is implanted subcutaneously near the abdominal midline using a 25 gauge needle. Test compounds are dosed as solutions in Ethanol/Ceremaphor EL/saline (12.5%: 12.5%:75%) at 30, 100, and 300 mg/kg po once daily starting on the day of implantation. Mice are euthanized 12 days post-implantation and the Matrigel pellets are harvested for analysis of hemoglobin content.

Hemoglobin Assay: The Matrigel pellets are placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete EDTA-free protease inhibitor cocktail [Mannheim, Germany]), and homogenized at 4° C. homogenates are incubated on ice for 30 minutes with shaking and centrifuged at 14K×g for 30 minutes at 4'C. Supernatants are transferred to chilled microfuge tubes and stored at 4° C. for hemoglobin assay.

Mouse hemoglobin (Sigma Chemical Co., St. Louis, Mo.) is suspended in autoclaved water (BioWhittaker, Inc, Walkersville, Md.) at 5 mg/ml. A standard curve is generated from 500 micrograms/ml to 30 micrograms/ml in Lysis Buffer (see above). Standard curve and lysate samples are added at 5 microliters/well in duplicate to a polystyrene 96-well plate. Using the Sigma Plasma Hemoglobin Kit (Sigma Chemical Co., St. Louis, Mo.), T M B substrate is reconstituted in 50 mls room temperature acetic acid solution. One hundred microliters of substrate is added to each well, followed by 100 microliters/well of Hydrogen Peroxide Solution at room temperature. The plate is incubated at room temperature for 10 minutes.

Optical densities are determined spectrophotometrically at 600 nm in a 96-well plate reader, SpectraMax 250 Microplate Spectrophotometer System (Molecular Devices, Sunnyvale, Calif.). Background Lysis Buffer readings are subtracted from all wells.

Total sample hemoglobin content is calculated according to the following equation:

Total Hemoglobin=(Sample Lysate Volume)×(Hemoglobin Concentration)

The average Total Hemoglobin of Matrigel samples without cells is subtracted from each Total Hemoglobin Matrigel sample with cells. Percent inhibition is calculated according to the following equation:

$$\% \text{ Inhibition} = \frac{(\text{Average Total Hemoglobin Drug-Treated Tumor Lysates}) \times 100}{(\text{Average Total Hemoglobin Non-Treated Tumore Lysates})}$$

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A method of blocking tumor angiogenesis in a human or other mammal comprising administering to a human or other mammal with a tumor of the liver an effective amount of the compound N-(4-chloro-3-(trifluoromethyl)phenyl)-N'-(4-(2-(N-methylcarbamoyl)-4-pyridyloxy)phenyl) urea of the formula below or a pharmaceutically acceptable salt thereof

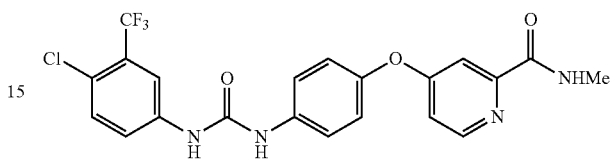

wherein the tumor of the liver is characterized by abnormal angiogenesis or hyperpermiability processes, which are mediated by KDR(VEGFR-2).

2. A method as in claim 1 wherein the compound N-(4-chloro-3-(trifluoromethyl)phenyl)-N'-(4-(2-(N-methylcarbamoyl)-4-pyridyloxy)phenyl) urea or a pharmaceutically acceptable salt thereof is administered simultaneously with another angiogenesis inhibiting agent to a human or other mammal with a tumor of the liver in the same formulation or in separate formulations.

3. A method as in claim 1 wherein the tumor that is treated is characterized by abnormal angiogenesis or hyperpermiability processes, which are not raf-mediated.

4. A method as in claim 1 wherein the tumor that is treated is characterized by abnormal angiogenesis or hyperpermiability processes, which are not p38-mediated.

5. The method of claim 1, wherein herein the effective amount of the compound N-(4-chloro-3-(trifluoromethyl)phenyl)-N'-(4-(2-(N-methylcarbamoyl)-4-pyridyloxy)phenyl) urea of the formula below is between 0.01 to 200 mg/Kg of total body weight

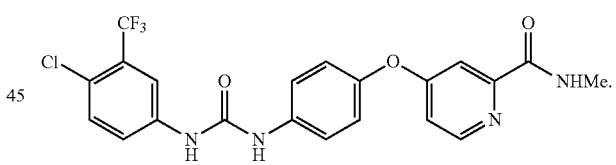

6. A method of blocking tumor angiogenesis in a human comprising administering to a human with a tumor of the liver an effective amount of the compound N-(4-chloro-3-(trifluoromethyl)phenyl)-N'-(4-(2-(N-methylcarbamoyl)-4-pyridyloxy)phenyl) urea tosylate, wherein the tumor of the liver is characterized by abnormal angiogenesis or hyperpermiability processes, which are mediated by KDR (VEGFR-2).

7. A method as in claim 6 wherein the tumor of the liver that is treated is characterized by abnormal angiogenesis or hyperpermiability processes, which are neither raf-mediated nor p38-mediated.

8. The method of claim 6, wherein the effective amount of the compound N-(4-chloro-3-(trifluoromethyl)phenyl)-N'-(4-(2-(N-methylcarbamoyl)-4-pyridyloxy)phenyl) urea tosylate is between 0.01 to 200 mg/Kg of total body weight.

* * * * *